United States Patent
Galvez

(10) Patent No.: US 9,133,255 B2
(45) Date of Patent: *Sep. 15, 2015

(54) PRODUCTS AND METHODS USING SOY PEPTIDES TO LOWER TOTAL AND LDL CHOLESTEROL LEVELS

(71) Applicant: SOY LABS, LLC, Linn, MO (US)

(72) Inventor: Alfredo Flores Galvez, West Sacramento, CA (US)

(73) Assignee: Soy Labs, LLC, Linn, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/069,013

(22) Filed: Oct. 31, 2013

(65) Prior Publication Data

US 2014/0057846 A1 Feb. 27, 2014

Related U.S. Application Data

(63) Continuation of application No. 12/441,384, filed as application No. PCT/US2007/078584 on Sep. 15, 2007, now Pat. No. 8,598,111.

(60) Provisional application No. 60/966,529, filed on Sep. 16, 2006, provisional application No. 61/007,925, filed on Jul. 17, 2007.

(51) Int. Cl.

| | |
|---|---|
| *A61K 38/00* | (2006.01) |
| *A61P 3/06* | (2006.01) |
| *A61K 38/16* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 14/415* | (2006.01) |
| *A61K 36/48* | (2006.01) |
| *A61K 45/06* | (2006.01) |

(52) U.S. Cl.
CPC .............. *C07K 14/415* (2013.01); *A61K 36/48* (2013.01); *A61K 38/005* (2013.01); *A61K 38/168* (2013.01); *A61K 45/06* (2013.01)

(58) Field of Classification Search
CPC ... A61K 36/48; A61K 38/005; A61K 38/168; A61K 45/06; C07K 14/415
See application file for complete search history.

(56) References Cited

U.S. PATENT DOCUMENTS

| 6,107,287 | A | 8/2000 | De Lumen et al. |
|---|---|---|---|
| 6,391,848 | B1 | 5/2002 | De Lumen et al. |
| 6,544,956 | B1 | 4/2003 | De Lumen et al. |
| 6,572,876 | B2 * | 6/2003 | Waggle et al. ............... 424/439 |
| 7,375,092 | B2 | 5/2008 | De Lumen et al. |
| 7,404,973 | B2 | 7/2008 | Konwinski et al. |
| 7,731,995 | B2 * | 6/2010 | Galvez ........................ 424/757 |
| 8,598,111 | B2 * | 12/2013 | Galvez ........................ 514/1.1 |
| 2002/0123093 | A1 | 9/2002 | Zannis et al. |
| 2003/0027765 | A1 | 2/2003 | Galvez |
| 2003/0064121 | A1 | 4/2003 | Konwinski et al. |
| 2003/0229038 | A1 | 12/2003 | De Lumen et al. |
| 2004/0071800 | A1 | 4/2004 | Waggle |
| 2007/0054031 | A1 | 3/2007 | Liu |

FOREIGN PATENT DOCUMENTS

| EP | 1017798 B1 | 5/2005 |
|---|---|---|
| WO | 99/15642 | 4/1999 |
| WO | 00/30665 A1 | 6/2000 |
| WO | 00/66625 | 9/2000 |
| WO | 01/72784 | 4/2001 |
| WO | 01/34808 A2 | 5/2001 |
| WO | 03/007976 A1 | 1/2003 |

OTHER PUBLICATIONS

Galvez, Alfredo F., et al., Chemopreventive Property of a Soybean Peptide (lunasin) That Binds to Deacetylated Histones and Inhibits Acetylation, Cancer Research (Oct. 15, 2001) 51, 7473-7478, USA.
Jeong, HJ, et al. "Characterization of Lunasin Isolated from Soybean" J. Agric. Food Chem. 2003, 51, 7901-7906.
Zhang X., Shu XO, Gao YT, Yang G., Li O, Li H, Jin F & Zheng W. Soy food consumption is associated with lower risk of coronary heart disease . . . J. Nutr. 133:2878 (2003).
Anderson JW, Johnstone BM & Cook Newell ME. Meta analysis of effects of soy protein intake on serum lipids in humans. N Eng J Med 333: 276 282 (1995).
Anthony MS, Clarkson TB, Hughes CL et at. Soybean isoflavones improve cardiovascular risk factors without affecting the . . . JNutri26: 43 50 (1996).
Arjmandi BH, Khan DA, Juma S & Svanborg A. "The ovarian hormone deficiency induced hypercholesterolomia is reversed by soy protein . . . "Nutr. Res. 17: 885 894 (1997).
Kirk EA, Sutherland P, Wang SA. "Dietary isoflavones reduce plasma cholesterol and atherosclerosis in C57BL/6 mice but not LDL . . . " J. Nutr. 128: 954 959 (1998).

(Continued)

*Primary Examiner* — Marcela M Cordero Garcia
(74) *Attorney, Agent, or Firm* — Kathryn P. Wilke

(57) ABSTRACT

Controlled studies demonstrate that products and related methods using soy related peptides lower total and LDL cholesterol levels in individuals. In one exemplary embodiment of the present disclosure, a product containing an effective amount of lunasin peptides that lowers cholesterol levels in an individual that consumes the lunasin peptides is provided. In another exemplary embodiment of the present disclosure, a composition containing an effective amount of lunasin peptides or lunasin peptide derivatives and one or more enzyme inhibitors is provided. In a related exemplary embodiment of the present disclosure, a method for lowering or reducing cholesterol levels in an individual is provided where a product containing an effective amount of lunasin peptides to an individual is provided and a claim that the product lowers or reduces cholesterol, total cholesterol, LDL cholesterol or lipid levels in an individual that consumes the composition is made.

45 Claims, 10 Drawing Sheets

(56) References Cited

OTHER PUBLICATIONS

Crouse JR, Morgan T, Terry JG. "A randomizing trial comparing the effect of casein with that of soy protein containing . . ."Arch Intern Med. 159: 2070 2076 (1999).

Wong WW, Smith EO, Stuff JE. "Cholesterol lowering effect of soy protein in normocholeslerolomic and hypercholesterolomic men." Am J Clin Nutr 68:1 385S 1389S (1998).

Greaves KA, Parks JS, Williams JK & Wagner JD "Intact dietary soy protein, but not adding an isoflavone rich soy extract to casein . . ."JNutr 129:1585 1592(1999).

Verrillo A, Teresa DE A, Giarrusso PC. "Soybean protein diets in the management of type II hyperlipoproteinaemia." Atherosclerosis, 54:321 (1985).

Kris Etherton P & West SG. Soy protein with or without isoflavones: in search of a cardioprotective mechanism of action. Am J Clin Nutr 81:5 6 (2005).

Anthony MS. Phytoestrogens and cardiovascular disease: Where's the meat? Arterioscler Thromb Vasc Biol 22: 1245 1257 (2002).

Vega Lopez S, Yeum K J, Leckler JL. Plasma antioxidant capacity in response to diets high in soy or animal protein with or without isoflavones. Am J Clin Nutr 81: 43 49 (2005).

Reynolds, K. et al. "A meta-analysis of the effect of soy protein supplementation on serum lipids." Am J Cardiol. Sep. 1, 2006;98(5):633-40.

Adams MR, Golden DL, Franke AA, Potter SM, Smith HS & Anthony MS. Dietary soy beta conglycinin (7S globulin) inhibits nhibits atherosclerosis in mice. J. Nutr. 134: 511 516 (2004).

Sacks, F.M. et al., "Soy protein, isoflavones and cardiovascular health." An American Heart Association Science Advisory . Circulation, On line publication, Feb. 21, 2006.

Galvez, A.F., Revilleza, M.J.R. & de Lumen, B.O. A novel methionine rich protein from soybean cotyledon: cloning and characterization of cDNA. Plant Physiol 114:1 567 (1997).

Galvez, A.F. & de Lumen, B.O. A soybean cDNA encoding a chromatin binding peptide inhibits mitosis of mammalian cells. Nature Biotech. 17: 495 500 (1999).

de Mejia E.G. et al., "Lunasin concentration in different soybean genotypes, commercial soy protein and isoflavone products." J. Agric. Food Chem. 52:5882-5887 (2004.).

Galvez, A.F. Chen, N., Macasieb, J., & de Lumen, B.O. Chemopreventive property of a soybean peptide. Cancer Res. 61:7473 7478 (2001).

De Pinho, R.A. The cancer chromatin connection. Nature 391: 533 536 (1998).

Park, Jae Ho, et al. "Contents and bioactivities of lunasin, Bowman-Birk inhibitor and isoflavones in soybean seed" J. Agric. Food Chem. 53:7686-7690 (2005).

Magbanua, M. et al., Nutrient Gene Interactions Involving Soy Peptide and Chemopreventive Genes in Prostate Epithelial Cells, in Nuritional Genomics Discovering the Path to Personalized Nutrition, J. Kaput and R. L. Rodriguez eds., Wiley and Sons, New Jersey (2005).

Bennett MK & Osborne TF. Nutrient regulation of gene expression by the sterol regulatory element binding proteins: Increased recruitment of gene specific coregulatory factors and selective hyperacetylation of histone H3 in vivo. PNAS 97:6340 6344 (2000).

Brown MS & Goldstein JL. Lowering plasma cholesterol by raising LDL receptors. Atherosclerosis Suppl 5: 57 59 (2004).

Sirtori CR, Gatti E, Mantero O, Conti F., et al. Clinical experience with the soybean protein diet in the treatment of hypercholesterolemia. Am J Clin Nutr. 32:1645 1658 (1979).

Descovich GC, Ceredi C., Gaddi A., Benassi MS, et al., Multicentre study of soybean protein diet for outpatient hyper cholesterolaemic patients. Lancet 2:709 712 (1980).

Lam, Y., Galvez, A., and de Lumen, B. O. "Lunasin suppresses E1A mediated transformation of mammalian cells . . ."Nutrition & Cancer, 47:88 94 (2003).

Coqueret, O. New roles for p21 and p27 cell cycle inhibitors: A function for each cell compartment? Trends in Cell Biology, 13:65 70, (2003).

Bruzzone, R. et al. Connections with connexins: The molecular basis of direct intercellular signaling. European Journ. Biochem., 238:1-27 (1996.).

Mullen E, et al. Soy isoflavones affect sterol regulatory element binding proteins (SREBPs) and SREBP regulated genes in HepG2 cells. J. Nutr. 134: 2942 2947 (2004).

Gherardi E., Thomas K, Le Cras TD, Fitzsimmons C, Moorby CD & Bowyer DE. "Growth requirements and expression of LDL receptor . . ."J Cell Sci. 103:531 539 (1992).

Brown MS & Goldstein JL. Lowering plasma cholesterol by raising LDL receptors. Atherosclerosis Suppl 5: 57-59 (2004).

Di Pietro CM & Liener IE. Soybean protease inhibitors in foods. Journal of Food Science 54: 606-609 (1989).

Jeong HJ, Lam Y & de Lumen BO."Barley lunasin suppresses ras-induced colony formation and inhibits core histone acetylation . . ."J Agric Food Chem. 50:5903-5908 (2002).

Jeong HJ, Jeong JB, Kim DS et al. The cancer preventive peptide lunasin from wheat inhibits core histone acetylation. Cancer Lett. 255:42-48 (2007).

Fratalli V. Soybean inhibitors.III. Properties of a low molecular weight soybean protease inhibitor. J Biol Chem 274:280 (1969).

Odani et al. Amino acid sequence of a soybean (Glycine max) seed polypeptide having a poly (L-aspartic acid) structure) J Biol Chem 262:10502-10505. (1987).

Kho, C.J. and de Lumen, B.O. Identification and isolation of methionine-cysteine rich protein fraction in soybean seed. Plant Foods for Human Nutrition 38: 287-296 (1988).

Revilleza M.J., Galvez A.F., Krenz D.C. and de Lumen B.O. An 8 kDa methionine-rich protein from soybean (Glycine max) cotyledon: Identification, purification and N-terminal sequence. J Agric Food Chem 44:2930-2935 (1996).

FDA Talk Paper "FDA approves new heatlh claim for soy protein and coronary heart disease," (online at http://222.scienceblog.co/community/older/archives /M/1/fda0589.htm, Oct. 20, 1999.).

* cited by examiner

FIGURE 1

2S Albumin Protein Containing Lunasin Subunit

Signal Peptide — Small subunit (Lunasin)

MTKFTILLISLLFCIAHTCSASKWQHQQDSCRKQLQGVNL

Chromatin-binding motif   Cell adhesion motif   Poly-aspartyl end                    Linker

TPC EKHIMEK QG RGDDDDDDDD NHILRTMGGRINYI

Large Subunit (methionine-rich protein)

RRNEGKDEDEEEGHMQKCCTEMSELRSPKCQCKALQKI

Nuclear localization sequence

MENQSEELEE KQKKK MEKELINLATMCRFGPMIQCDLSSDD

HMG-CoA reductase Expression In Lunasin-Treated Cholesterol-Free Media

LDL Receptor Expression In Lunasin-Treated Cholesterol-Free Media

Sp1 Expression In Lunasin Treated Growth Media And Cholesterol Free Media

UnTrt  Temp (-)  A    B    C    D    E    F

A = LeSC
B = LeSC + SF
C = LeSC + SF digested
D = LeSC digested
E = SPI digested
F = SC digested

| temp (-) | NaB (+) | - syn L | +syn L | A | A Dig | B | B Dig |
|---|---|---|---|---|---|---|---|
| 1.0 | 2.2 | 1.8 | 1.3 | 1.15 | 1.6 | 1.15 | 1.0 |

A = LeSC
B = LeSC + SF

Lunasin immunostaining

SEQUENCE LISTING

```
<160> NUMBER OF SEQ ID NOS: 2

<210> SEQ ID NO 1
<211> LENGTH: 157
<212> TYPE: PRT
<213> ORGANISM: Glycine max

<400> SEQUENCE: 1

Met Thr Lys Phe Thr Ile Leu Leu Ile Ser Leu Leu Phe Cys Ile Ala
1               5                   10                  15

His Thr Cys Ser Ala Ser Lys Trp Gln His Gln Gln Asp Ser Cys Arg
            20                  25                  30

Lys Gln Leu Gln Gly Val Asn Leu Thr Pro Cys Glu Lys His Ile Met
        35                  40                  45

Glu Lys Ile Gln Gly Arg Gly Asp Asp Asp Asp Asp Asp Asp Asp Asp
    50                  55                  60
```

```
Asn His Ile Leu Arg Thr Met Gly Gly Arg Ile Asn Tyr Ile Arg Arg
 65                  70                  75                  80

Asn Glu Gly Lys Asp Glu Asp Glu Glu Gly His Met Gln Lys Cys
                 85                  90                  95

Cys Thr Glu Met Ser Glu Leu Arg Ser Pro Lys Cys Gln Cys Lys Ala
             100                 105                 110

Leu Gln Lys Ile Met Glu Asn Gln Ser Glu Glu Leu Glu Glu Lys Gln
         115                 120                 125

Lys Lys Lys Met Glu Lys Glu Leu Ile Asn Leu Ala Thr Met Cys Arg
         130                 135                 140

Phe Gly Pro Met Ile Gln Cys Asp Leu Ser Ser Asp Asp
145                 150                 155

<210> SEQ ID NO 2
<211> LENGTH: 43
<212> TYPE: PRT
<213> ORGANISM: Glycine max

<400> SEQUENCE: 2

Ser Lys Trp Gln His Gln Gln Asp Ser Cys Arg Lys Gln Leu Gln Gly
 1               5                  10                  15

Val Asn Leu Thr Pro Cys Glu Lys His Ile Met Glu Lys Ile Gln Gly
             20                  25                  30

Arg Gly Asp Asp Asp Asp Asp Asp Asp Asp
         35                  40
```

PRODUCTS AND METHODS USING SOY PEPTIDES TO LOWER TOTAL AND LDL CHOLESTEROL LEVELS

RELATED APPLICATIONS

This application is a continuation of application Ser. No. 12/441,384, which is the National Stage of International Application No. PCT/US07/78584, filed Sep. 15, 2007, (which is incorporated by reference herein in its entirety for all purposes), which claims the benefit under 35 U.S.C. §119 (e) of U.S. Provisional Application Ser. No. 60/966,529, filed Sep. 16, 2006 (known as U.S. patent application Ser. No. 11/532,526 at the time the PCT application claimed priority to it), (which is incorporated by reference herein in its entirety for all purposes), and which claims the benefit under 35 U.S.C. §119(e) of U.S. Provisional Application Ser. No. 61/007,925, filed Jul. 17, 2007 (known as U.S. patent application Ser. No. 11/879,249 at the time the PCT application claimed priority to it), (which is incorporated by reference herein in its entirety for all purposes).

U.S. application Ser. No. 11/532,528, U.S. application Ser. No. 12/441,384, International Application No. PCT/US07/78584, filed Sep. 15, 2007, U.S. Provisional Application No. 60/966,529, filed Sep. 16, 2006 (formerly known as U.S. patent application Ser. No. 11/532,526), and U.S. Provisional Application No. 61/007,925, filed Jul. 17, 2007 (formerly known as U.S. patent application Ser. No. 11/879,249) are all incorporated by reference herein in their entirety for all purposes.

FIELD OF THE INVENTION

This invention relates generally to compositions and methods for treatment of cholesterol related conditions in individuals. More specifically, this invention relates to a class of peptides that provide individuals with a variety of health related benefits and compositions comprising them. More specifically, the present invention relates to novel compositions comprising soy peptides, methods of using these compositions to lower total and LDL cholesterol levels in individuals, and methods of making compositions comprising them.

BACKGROUND OF THE INVENTION

Coronary heart disease (CHD) is a major health problem in the US, with death rates exceeding 1 million annually. Risk factors include cigarette smoking and hypertension, but elevated plasma cholesterol has been implicated as the primary risk factor for CHD. High total cholesterol and low-density lipoprotein (LDL) cholesterol levels contribute to the formation of atherosclerotic plaques and eventually to thrombosis or myocardial infarction. Hence, management of cholesterol levels is an essential part of prevention and treatment strategies to reduce the incidence, mortality and morbidity of coronary heart disease.

There is substantial epidemiological evidence that dietary factors, such as consumption of certain soy proteins can help manage cholesterol levels and reduce CHD risk in certain individuals. Some epidemiological studies have shown that soy food consumption is linked with a decreased risk of cardiovascular disease in some Asian populations (1). More recently, a large-scale 3-year cohort study of 75,000 Chinese women have shown a dose-response relationship between soy food intake and reduced risk of coronary heart disease, especially nonfatal myocardial infarction (2). Meta-analysis results from 38 clinical studies including 730 research volunteers, showed that soy protein intake was associated with 9.3% reduction of serum cholesterol, a 12.9% reduction in serum LDL-cholesterol, a 10.5% reduction of serum triglycerides, and a non-significant increase in high density lipoprotein (HDL) levels (3). The clinical results of the experiments involving soy protein has prompted the Food and Drug Administration (FDA) to allow a health claim on food labels stating that 25 grams of soy protein as part of a daily diet low in saturated fat and cholesterol may reduce the risk of heart disease.

The candidate components of soy that could contribute to its hypocholesterolemic effect include soy proteins and its non-protein components, saponins and isoflavones, genistein and daidzein. Unfortunately, the body of experimental data indicates that it is still unclear which of these components provides hypocholesterolemic effects. Many have hypothesized that soy isoflavones are responsible for the reducing cholesterol in animals. In fact, numerous studies have focused on the role of soy isoflavones in reducing cholesterol levels in animals (4-6) and humans (7, 8). Interestingly, these and other studies show that soy isoflavones do not provide any cholesterol lowering effects. For example, in one study, when isoflavone-rich extract of soy was fed to cynomolgus monkeys in the absence of soy protein, it did not produce any cholesterol lowering effects (9).

In some studies, when soy protein was simply added to the animal's diet, significant reductions in cholesterol were observed (10). Concerns about a viable cardioprotective mechanism of action attributable to isoflavones (11-13) have also tempered the enthusiasm about the role of isoflavones in reducing CHD risk. Saponins, a structurally diverse group of triterpene or steroid glycosides, have also been proposed as possible soy component responsible for its hypocholesterolemic activity (14). However, there are no convincing animal or human studies as well as a viable mechanism of action to indicate that saponins are responsible for the hypocholesterolemic activity of soy. The same is true with 7S globulins, a major soy storage protein, which is found to inhibit atherosclerosis in mice, but did not show hypocholesterolemic effects (15).

In February 2006, the American Heart Association released a scientific advisory report on soy protein, isoflavones and cardiovascular health by analyzing recent clinical data published since the FDA-approved health claim (16). Among 19 studies of soy isoflavones, the American Heart Association found that isoflavones, on average, have no effect on Low Density Lipoprotein cholesterol ("LDL cholesterol") or other lipid risk factors. The report concludes that, "A very large amount of soy protein, more than half the daily protein intake, may lower LDL cholesterol by a few percentage points when it replaces dairy protein of a mixture of animal proteins. The evidence favors soy protein rather than soy isoflavones as the responsible nutrient. However, at this time, the possibility cannot be ruled out that another component of soybeans, could be the active factor. Therefore it still is not clear what component or components of soy protein provide beneficial cholesterol lowering effects that reduce the risk of CHD. As a result, present methods of lowering cholesterol using soy protein have provided varying results that are neither targeted nor highly effective.

An additional drawback to use of the soy products described in the above clinical trials and endorsed by the FDA is the large amount (25 mg/day) of soy product that is required to obtain a beneficial result. It would be desirable to have a more concentrated composition, making it easier to obtain sufficient levels of the desired portion of the soy product as well as making preparing and packaging of such soy products more feasible.

Accordingly, there exists a need for improved compositions and related methods for effectively reducing total and LDL cholesterol in individuals. The present invention provides these and other related benefits.

DEFINITIONS

To facilitate an understanding of the invention, a number of terms and phrases are defined below. Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The general techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted.

As used herein, the singular form "a", "an", and "the" includes plural references unless indicated otherwise. For example, "a" protease enzyme inhibitor includes one or more protease enzyme inhibitors.

As used herein "ug" is an abbreviation for microgram and "uM" is an abbreviation for micromole.

As used herein, "biological activity" and "bioactivity" refer to the in vivo activities of a compound or physiological responses that result upon in vivo administration of a compound, composition, or other mixture. Biological activity, thus, encompasses therapeutic effects and pharmaceutical activity of such compounds, compositions and mixtures. Biological activities may be observed and measured in in vitro systems designed to test or use such activities also.

As used herein, the term "biologically active" refers to a molecule having structural, regulatory and or biochemical functions of a naturally occurring lunasin molecule.

As used herein, a "combination" refers to any association between two or among more items.

As used herein, the term "suffering from disease" refers to a subject (e.g., a human) that is experiencing a particular disease. It is not intended that the present invention be limited to any particular signs or symptoms, nor disease. Thus, it is intended that the present invention encompass subjects that are experiencing any range of disease (e.g., from sub-clinical manifestation to full-blown disease) wherein the subject exhibits at least some of the indicia (e.g., signs and symptoms) associated with the particular disease.

As used herein, the terms "disease" "disorder" and "pathological condition" are used interchangeably to describe a state, signs, and/or symptoms that are associated with any impairment of the normal state of a living animal or of any of its organs or tissues that interrupts or modifies the performance of normal functions, and may be a response to environmental factors (such as malnutrition, industrial hazards, or climate), to specific infective agents (such as worms, bacteria, or viruses), to inherent defect of the organism (such as various genetic anomalies, or to combinations of these and other factors.

As used herein, the term "effective amount" refers to the amount of a composition (e.g., comprising Lunasin) sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment (e.g., compositions of the present invention) to a subject (e.g., a subject or in vivo, in vitro, or ex vivo cells, tissues, and organs) and/or to direct, instruct, or advise the use of the composition for any purpose (preferably, for a purpose described herein). Where the administration of one or more of the present compositions is directed, instructed or advised, such direction may be that which instructs and/or informs the user that use of the composition may and/or will provide one or more of the benefits described herein.

Exemplary routes of administration to the human body can be through the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

Administration which is directed may comprise, for example, oral direction (e.g., through oral instruction from, for example, a physician, health professional, sales professional or organization, and/or radio or television media (i.e., advertisement) or written direction (e.g., through written direction from, for example, a physician or other health professional (e.g., scripts), sales professional or organization (e.g., through, for example, marketing brochures, pamphlets, or other instructive paraphernalia), written media (e.g., internet, electronic mail, or other computer-related media), and/or packaging associated with the composition (e.g., a label present on a package containing the composition). As used herein, "written" includes through words, pictures, symbols, and/or other visible descriptors. Such direction need not utilize the actual words used herein, but rather use of words, pictures, symbols, and the like conveying the same or similar meaning are contemplated within the scope of this invention.

As used herein, the terms "co-administration" and "co-administering" refer to the administration of at least two agent(s) (e.g., composition comprising Lunasin and one or more other agents—e.g., a protease enzyme inhibitor) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "treatment" or grammatical equivalents encompasses the improvement and/or reversal of the symptoms of disease (e.g., heart disease). A composition which causes an improvement in any parameter associated with disease when used in the screening methods of the instant invention may thereby be identified as a therapeutic composition. The term "treatment" refers to both therapeutic treatment and prophylactic or preventative measures. For example, those who may benefit from treatment with compositions and methods of the present invention include those already with a disease and/or disorder (e.g., elevated cholesterol levels) as well as those in which a disease and/or disorder is to be prevented (e.g., using a prophylactic treatment of the present invention).

As used herein, the term "at risk for disease" refers to a subject (e.g., a human) that is predisposed to experiencing a particular disease. This predisposition may be genetic (e.g., a particular genetic tendency to experience the disease, such as heritable disorders), or due to other factors (e.g., age, weight, environmental conditions, exposures to detrimental compounds present in the environment, etc.). Thus, it is not intended that the present invention be limited to any particular risk, nor is it intended that the present invention be limited to any particular disease.

As used herein, the terms "individual," "host," "subject" and "patient" refer to any animal, including but not limited to, human and non-human animals (for example, without limitation, primates, dogs, cats, cows, horses, sheep, rodents, poultry, fish, crustaceans, etc.) that is studied, analyzed, tested, diagnosed or treated. As used herein, the terms "individual," "host," "subject" and "patient" are used interchangeably, unless indicated otherwise.

As used herein, the term "antibody" (or "antibodies") refers to any immunoglobulin that binds specifically to an antigenic determinant, and specifically binds to proteins identical or structurally related to the antigenic determinant that stimulated their production. Thus, antibodies can be useful in assays to detect the antigen that stimulated their production. Monoclonal antibodies are derived from a single clone of B lymphocytes (i.e., B cells), and are generally homogeneous in structure and antigen specificity. Polyclonal antibodies originate from many different clones of antibody-producing cells, and thus are heterogenous in their structure and epitope specificity, but all recognize the same antigen. Also, it is intended that the term "antibody" encompass any immunoglobulin (e.g., IgG, IgM, IgA, IgE, IgD, etc.) obtained from any source (e.g., humans, rodents, non-human primates, lagomorphs, caprines, bovines, equines, ovines, etc.).

As used herein, the term "antigen" is used in reference to any substance that is capable of being recognized by an antibody.

As used herein, the terms "Western blot," "Western immunoblot" "immunoblot" and "Western" refer to the immunological analysis of protein(s), polypeptides or peptides that have been immobilized onto a membrane support. The proteins are first resolved by polyacrylamide gel electrophoresis (i.e., SDS-PAGE) to separate the proteins, followed by transfer of the protein from the gel to a solid support, such as nitrocellulose or a nylon membrane. The immobilized proteins are then exposed to an antibody having reactivity towards an antigen of interest. The binding of the antibody (i.e., the primary antibody) is detected by use of a secondary antibody that specifically binds the primary antibody. The secondary antibody is typically conjugated to an enzyme that permits visualization of the antigen-antibody complex by the production of a colored reaction product or catalyzes a luminescent enzymatic reaction (e.g., the ECL reagent, Amersham).

The term "compound" refers to any chemical entity, pharmaceutical, drug, and the like that can be used to treat or prevent a disease, illness, sickness, or disorder of bodily function. Compounds comprise both known and potential therapeutic compounds. Compounds comprise polypeptides such as those described herein.

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent (e.g., Lunasin) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., alveolar, buccal, lingual, masticatory, or nasal mucosa, and other tissues and cells that line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975), incorporated herein by reference).

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "gene expression" and "expression" refer to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refer to regulation that increases and/or enhances the production of gene expression products (e.g., RNA or protein), while "down-regulation" or "repression" refer to regulation that decrease production. Molecules (e.g., transcription factors) that are involved in up-regulation or down-regulation are often called "activators" and "repressors," respectively.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein "amino acid" refers to any of the naturally occurring amino acids having the standard designations listed in Table 1, below. It also refers to those known synthetic amino acids. Unless otherwise indicated, all amino acid sequences listed in this disclosure are listed in the order from the amino terminus to the carboxyl terminus. As used herein, the abbreviations for any protective groups, amino acids and other compounds, are in accord with their common usage, recognized abbreviations, or the IUPAC-IUB Commission on Biochemical Nomenclature, unless otherwise indicated (see Biochemistry 11: 1726 (1972)). As used herein, amino acid residues are represented by the full name thereof, by the three letter code corresponding thereto, or by the one-letter code corresponding thereto, as indicated in the following table:

TABLE 1

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |

TABLE 1-continued

| Full Name | Three-Letter Code | One-Letter Code |
| --- | --- | --- |
| Proline | Pro | P |
| Phenylalanine | Phe | F |
| Tryptophan | Trp | W |

As used herein, the terms "peptide," "polypeptide" and "protein" all refer to a primary sequence of amino acids that are joined by covalent "peptide linkages." In general, a peptide consists of a few amino acids, typically from 2-50 amino acids. The term "polypeptide" encompasses peptides and proteins, wherein the term "protein" typically refers to large polypeptides and the term "peptide" typically refers to short polypeptides. In some embodiments, the peptide, polypeptide or protein is synthetic, while in other embodiments, the peptide, polypeptide or protein is recombinant or naturally occurring. A "synthetic" peptide is a peptide that is produced by artificial means in vitro (i.e., was not produced in vivo). The term "peptide" further includes modified amino acids (whether naturally or non-naturally occurring), such modifications including, but not limited to, phosphorylation, glycosylation, pegylation, lipidization and methylation.

An "isolated peptide" is a peptide which has been substantially separated from components (e.g., DNA, RNA, other proteins and peptides, carbohydrates and lipids) which naturally accompany it in a cell.

As applied to polypeptides, the term "substantial identity" means that two peptide sequences, when optimally aligned, such as by the programs GAP or BESTFIT using default gap weights, share at least 80% sequence identity, preferably at least 90% sequence identity, more preferably at least 95% sequence identity or more (e.g., 99% sequence identity). Preferably, residue positions which are not identical differ by conservative amino acid substitutions.

The phrase "functionally equivalent" means that the variant, analogue or fragment of a polypeptide retains a desired biological activity in common with the lunasin polypeptide. In at least one embodiment of the present invention, the desired biological activity in common with lunasin is biological activity related to the control, stabilization, or reduction in production or existing levels of cholesterol, LDL cholesterol, total cholesterol, or lipids. Preferably, a given quantity of the analogue, variant or fragment is at least 10%, preferably at least 30%, more preferably at least 50, 60, 80, 90, 95 or 99% as effective as an equivalent amount of the naturally occurring lunasin from which the analogue, variant or fragment is derived. Determination of the relative efficacy of the analogue, variant or fragment can readily be carried out by utilizing a prescribed amount of the analogue, variant or fragment in the one or more of the assay methods of the invention and then comparing the ability of the analogue, variant or fragment to naturally occurring lunasin in tests that measure the ability of the sample to inhibit the acetylation of histone H3, or to effect the expression of HMG Co-A reductase, Sp1 or LDL-receptor.

The term "analogue" as used herein with reference to a polypeptide means a polypeptide which is a derivative of the polypeptide of the invention, which derivative comprises addition, deletion, and/or substitution of one or more amino acids, such that the polypeptide retains substantially the same function as the lunasin polypeptide identified below.

The term "fragment" refers to a polypeptide molecule that is a constituent of the full-length lunasin polypeptide and possesses qualitative biological activity in common with the full-length lunasin polypeptide. The fragment may be derived from the full-length lunasin polypeptide or alternatively may be synthesized by some other means, for example chemical synthesis. By reference to "fragments" it is intended to encompass fragments of a protein that are of at least 5, preferably at least 10, more preferably at least 20 and most preferably at least 30, 40 or 50 amino acids in length and which are functionally equivalent to the protein of which they are a fragment.

The term "variant" as used herein refers to a polypeptide which is produced from a nucleic acid encoding lunasin, but differs from the wild type lunasin in that it is processed differently such that it has an altered amino acid sequence. For example a variant may be produced by an alternative splicing pattern of the primary RNA transcript to that which produces wild type lunasin.

Analogues and variants are intended to encompass proteins having amino acid sequence differing from the protein from which they are derived by virtue of the addition, deletion or substitution of one or more amino acids to result in an amino acid sequence that is preferably at least 60%, more preferably at least 80%, particularly preferably at least 85, 90, 95, 98, 99 or 99.9% identical to the amino acid sequence of the original protein. The analogues or variants specifically include polymorphic variants and interspecies analogues. The analogues and variants of the present invention further may have "conservative" changes, wherein a substituted amino acid has similar structural or chemical properties. One type of conservative amino acid substitution refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays such as those described in the Examples section below.

The term "conservative amino acid substitution" as used herein refers to a substitution or replacement of one amino acid for another amino acid with similar properties within a polypeptide chain (primary sequence of a protein). For example, the substitution of the charged amino acid glutamic acid (Glu) for the similarly charged amino acid aspartic acid (Asp) would be a conservative amino acid substitution.

As used herein "lunasin" refers to the natural, synthetically or recombinantly obtained soybean lunasin polypeptide set forth in (SEQ. ID. 2). Additional description of the Lunasin peptide and an evaluation of various functionally equivalent fragments and analogues appear in U.S. Pat. No. 6,107,287, U.S. Pat. No. 6,544,956, US Patent Application 2003/0229038, filed Nov. 22, 2002, U.S. Pat. No. 6,391,848, U.S. patent application Ser. No. 10/252,256, filed Sep. 23, 2002, and U.S. patent application Ser. No. 10/302,633, filed Nov. 22, 2002, all of which are hereby incorporated by reference herein in their entirety for all purposes. These disclosures will guide one skilled in the art in identifying functionally equivalent and biologically active fragments, variants and analogues of lunasin.

As used herein "lunasin enriched" refers to compositions containing biologically active levels of naturally occurring lunasin, or a naturally occurring analogue of lunasin, that is at a concentration greater than that at which lunasin is found in the material used as the source of that lunasin or analogue. As used herein "lunasin enriched seed extract" refers to compositions containing biologically active levels of naturally occurring lunasin, or a naturally occurring analogue of lunasin, that is at a concentration at least twice than that at which lunasin is naturally found in the source seed. Without limiting the invention to any particular source of the compositions of the present invention, lunasin enriched compositions can be obtained from soybean, wheat, barley, soy isolates, soy concentrates, or other soy derived products, whether or not commercially obtained.

As used herein "lunasin protecting soy flour" refers to soy flour compositions comprising soy flour and an amount of a protease inhibitor sufficient to protect lunasin, or a analogue, variant or fragment thereof, from complete digestion, wherein the compositions do not have levels of anti-nutritional elements that would cause an adverse effect in an individual who ingested them.

As used herein "digested" refers to the treatment of a polypeptide with a digestive material that breaks it down into its component amino acids. Examples of digestive materials that can be used are well known in the art, and include, without limitation, pancreatin and other proteases such as trypsin, chymotrypsin, pepsin, Proteinase K, thermolysin, thrombin, Arg-C proteinase, Asp-N endopeptidase, AspN endopeptidase+N-terminal Glu, BNPS-Skatole, CNBr, clostripain, formic acid, glutamyl endopeptidase, iodosobenzoic acid, LysC, LysN, NTCB (2-nitro-5-thiocyanobenzoic acid), and Staphylococcal peptidase.

As used herein "partially digested biologically active" in relation to a polypeptide refers to the treatment of a polypeptide with a digestive material under conditions that increase the biological activity of the polypeptide.

The phrase "combination therapy" embraces the administration of a composition of the present invention in conjunction with another pharmaceutical agent that is indicated for treating or preventing a disorder, as part of a specific treatment regimen intended to provide a beneficial effect from the co-action of these therapeutic agents.

Referenced herein are trade names for components including various ingredients utilized in the present invention. The inventors herein do not intend to be limited by materials under a certain trade name. Equivalent materials (e.g., those obtained from a different source under a different name or reference number) to those referenced by trade name may be substituted and utilized in the descriptions herein.

The compositions herein may comprise, consist essentially of, or consist of any of the elements as described herein.

The practice of the present invention will employ, unless otherwise indicated, conventional techniques of molecular biology (including recombinant techniques), microbiology, cell biology, biochemistry, immunology, and protein kinetics, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); and Mass isotopomer distribution analysis at eight years: theoretical, analytic and experimental considerations by Hellerstein and Neese (Am J Physiol 276 (Endocrinol Metab. 39) E1146-E1162, 1999), all of which are incorporated herein by reference in their entirety. Furthermore, procedures employing commercially available assay kits and reagents will typically be used according to manufacturer-defined protocols unless otherwise noted.

SUMMARY OF THE INVENTION

The present disclosure relates to products and related methods using soy related peptides to lower total and LDL cholesterol levels in individuals.

In one embodiment, the present invention provides methods for lowering cholesterol levels in an individual, comprising: providing an individual desiring or needing to lower cholesterol levels and, a composition comprising a compound selected from the group consisting of the peptide of SEQ ID NO 2 and a functionally equivalent variant, fragment or analogue of said peptide; and administering said composition to said subject. In certain embodiments the compound is obtained from soybean, wheat or barley, or by producing, extracting and purifying said compound using recombinant DNA techniques or by synthetic polypeptide production. In certain embodiments, the individual is a human. In certain embodiments the administering comprises oral ingestion of the composition, and in certain embodiments the composition is in the form of a capsule, tablet, powder, semi-solid formulation, liquid, gel, suspension, or aerosol spray. In certain embodiments the composition further comprises soy flour. In certain embodiments the soy flour is a lunasin protecting soy flour. In certain preferred embodiments the composition further comprises chymotrypsin inhibitor. In certain embodiments the compound is administered to said individual at between 0.05 mg/kg and 50 mg/kg daily. In certain embodiments, the individual is at risk for atherosclerosis, arterial sclerosis, myocardial infarction, heart attack, diabetes, coronary heart disease, angina pectoris or unstable angina.

In another embodiment, this invention provides methods for treating or preventing cardiovascular disease comprising: providing an individual suffering from or at risk of developing cardiovascular disease, and, a composition comprising a compound selected from the group consisting of the peptide of SEQ ID NO 2 and a functionally equivalent variant, fragment or analogue of said peptide; and administering said composition to said subject. In certain embodiments the compound is obtained from soybean, wheat or barley, or by producing, extracting and purifying said compound using recombinant DNA techniques or by synthetic polypeptide production, or wherein said individual is a human. In certain embodiments the administering comprises oral ingestion of the composition, and in certain embodiments the composition is in the form of a capsule, tablet, powder, semi-solid formulation, liquid, gel, suspension, or aerosol spray. In certain embodiments the composition further comprises soy flour. In certain preferred embodiments the composition further comprises chymotrypsin inhibitor. In certain embodiments the compound is administered to said individual at between 0.05 mg/kg and 50 mg/kg daily. In certain embodiments, the individual is at risk for atherosclerosis, arterial sclerosis, myocardial infarction, heart attack, diabetes, coronary heart disease, angina pectoris or unstable angina.

In another embodiment this invention provides compositions comprising a partially digested biologically active peptide of SEQ ID NO 1. In certain embodiments, the composition also comprises a chymotrypsin inhibitor. In certain embodiments the composition further comprises soy flour.

In another embodiment this invention provides methods of treating the skin of an individual, comprising: a) providing i) an individual and ii) a composition of claim 23, and b) administering the composition of claim 23 topically to the individual.

In another embodiment this invention provides compositions comprising lunasin enriched seed extract and soy flour. In certain embodiments, the ratio by weight of lunasin enriched seed extract and soy flour is between a) 90% lunasin enriched seed extract to 10% soy flour and b) 60% lunasin enriched seed extract to 40% soy flour, preferably approximately 70% lunasin enriched seed extract to 30% soy flour. In certain embodiments, soy flour comprises a chymotrypsin inhibitor. In certain embodiments, lunasin is present in the compositions in a concentration of between 0.5% and 5% by weight of the composition.

In another embodiment this invention provides methods of improving lunasin biological activity comprising: a) providing lunasin, and b) partially digesting said lunasin. In certain embodiments, soy flour is present while lunasin is being digested.

In another embodiment this invention provides methods for lowering or reducing cholesterol levels in an individual, comprising: providing a product containing a peptide selected from the group consisting of the peptide of SEQ ID NO 2 and a functionally equivalent fragment, variant or analogue of SEQ ID NO 2; and claiming that the product reduces or maintains cholesterol, total cholesterol, LDL cholesterol or lipid levels in an individual that consumes the composition. In certain embodiments the peptide is obtained from soybean, wheat or barley, or by producing, extracting and purifying said compound using recombinant DNA techniques or by synthetic polypeptide production. In certain embodiments, the individual is a human. In certain embodiments the administering comprises oral ingestion of the composition, and in certain embodiments the composition is in the form of a capsule, tablet, powder, semi-solid formulation, liquid, gel, suspension, or aerosol spray. In certain embodiments the composition further comprises soy flour. In certain preferred embodiments the composition further comprises chymotrypsin inhibitor. In certain embodiments the composition is administered to said individual at between 25 mg/kg and 100 mg/kg daily. In certain embodiments, the individual is at risk for atherosclerosis, arterial sclerosis, myocardial infarction, heart attack, diabetes, coronary heart disease, angina pectoris or unstable angina.

In another embodiment, the present invention provides method for reducing or maintaining cholesterol levels, comprising: providing to a human in need thereof a biologically active amount of the peptide of SEQ ID NO 2.

In one exemplary embodiment of the present invention, a product containing an effective amount of lunasin peptides that lowers cholesterol levels in an individual that consumes the product is provided.

In another exemplary embodiment of the present invention, a composition containing an effective amount of lunasin peptides or lunasin peptide derivatives and one or more enzyme inhibitors that act together to lower cholesterol levels in an individual that consumes the composition is provided.

In yet another exemplary embodiment of the present invention, a method for lowering or reducing cholesterol levels in an individual is provided. The method includes providing a product containing an effective amount of lunasin peptides to an individual and claiming that the product lowers, reduces or maintains cholesterol, total cholesterol, LDL cholesterol or lipid levels in an individual that consumes the composition.

In an aspect of at least one embodiment of the present invention, the effective amount of lunasin peptides and/or lunasin derivative peptides that lowers cholesterol levels in an individual is 25 mg to 100 mg daily, assuming on average soy protein contains 0.1% lunasin and that at least 25 gm of soy protein a day is clinically proven to reduce LDL cholesterol in humans.

In another aspect of at least one embodiment of the present invention, the cholesterol levels lowered in the individual are LDL and total cholesterol levels.

In yet another aspect of at least one embodiment of the present invention, the lunasin peptides include lunasin peptides or lunasin peptide derivatives.

In yet another aspect of at least one embodiment of the present invention, the lunasin peptides are obtained from soy.

In yet another aspect of at least one embodiment of the present invention, the lunasin peptides are obtained from soy and other seed bearing plants.

In yet another aspect of at least one embodiment of the present invention, the lunasin peptides or lunasin peptide derivatives are obtained by producing, extracting and purifying lunasin peptides or lunasin peptide derivatives using recombinant DNA techniques.

In yet another aspect of at least one embodiment of the present invention, the lunasin peptides or lunasin peptide derivatives are obtained by synthetic sequencing.

In yet another aspect of at least one embodiment of the present invention, the one or more enzyme inhibitors include one or more trypsin inhibitors.

In yet another aspect of at least one embodiment of the present invention, the assays described in the examples that follow can be employed to screen lunasin isolates, concentrates, extracts, analogues, fragments and variants to confirm desired activity prior to using them in methods of the present invention. The present invention encompasses methods of screening soy isolates, concentrates and extracts as well as variants, fragments and analogues of lunasin to measure activity in order to identify those with preferred activity for use in the compositions and methods of the present invention, whereby an experiment similar to the one described herein is performed using lunasin analogues, fragments or variants in place of lunasin, thereby teaching one skilled in the art simple methods of screening the activity levels of analogues, variants and fragments of lunasin for use in the present invention.

DESCRIPTION OF THE FIGURES

The above-mentioned features and objects of the present disclosure will become more apparent with reference to the following description taken in conjunction with the accompanying drawings wherein like reference numerals denote like elements and in which:

FIG. 1 shows the 2S albumin protein encoded by Gm2S 1 cDNA (SEQ ID NO 1). Arrows indicate endoproteolytic sites that give rise to small subunit (lunasin) (SEQ ID NO 2) and the large subunit (methionine rich protein). Important regions in both subunits are indicated.

GENERAL DESCRIPTION OF THE PREFERRED EMBODIMENTS

Figure 2:
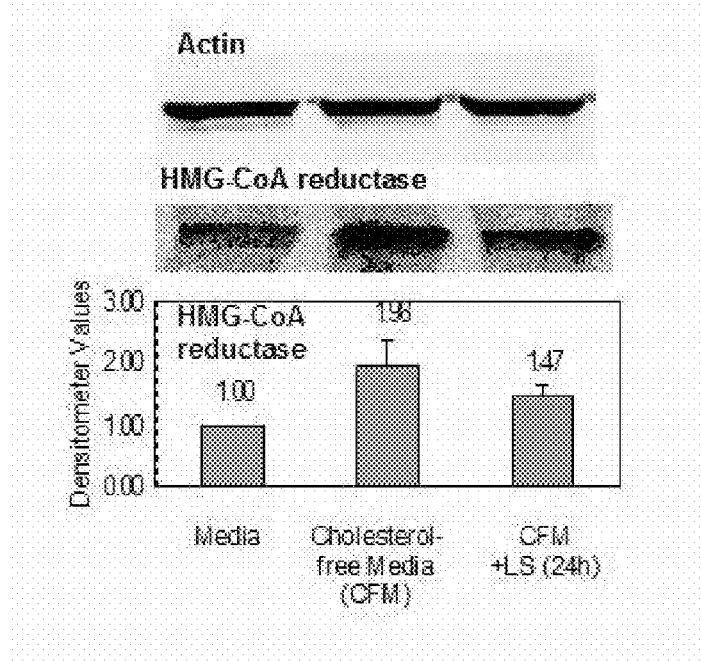
FIG. 2 is a photograph of a Western blot analysis (top) and a table (below) showing densitometer values indicating the relative levels of expression of HMG-CoA reductase in HepG2 cells that were (CFM+LS (24)) or were not (CFM) treated with lunasin for 24 hours prior to incubation in cholesterol free media (CFM) for 24 hours to activate sterol regulatory element binding proteins (SREBP.) After incubations, total protein was extracted and 10 ug protein was loaded onto 10% Tris-glycine gels, electroblotted onto nitrocellulose membrane, and immunostained with primary antibodies raised against HMG-CoA reductase and actin (to show equal loading of proteins.) Spot densitometer values represent mean and standard deviation of data from three separate experiments.

This invention relates generally to compositions and methods for treatment of cholesterol related conditions in individuals. More specifically, this invention relates to a class of peptides that provide individuals with a variety of health related benefits and compositions comprising them. More specifically, the present invention relates to novel compositions comprising soy peptides, methods of using these compositions to lower total and LDL cholesterol levels in individuals, and methods of making compositions comprising them.

Lunasin

Lunasin is a recently discovered bioactive component in soybean (*glycine max*) with a novel chromatin-binding property and epigenetic effects on gene expression (17, 18). Lunasin is the small subunit peptide of a cotyledon-specific 2S albumin. FIG. 1 shows the 2S albumin protein (SEQ. ID. NO. 1) and the small lunasin subunit (SEQ. ID. NO. 2). The lunasin soy peptide is heat stable, water soluble and found in significant amounts in select soy protein preparations, and significant guidance is provided in the literature on selection of sources of soy and soy products for isolation or concentration of lunasin (19).

Lunasin is herein identified as an active component of soy having hypocholesterolemic effects. Compositions and methods of making and using lunasin for, among other things, the reduction of cholesterol, are also described.

This discovery solves several problems that had, until now, made the use of soy products for cholesterol reduction difficult. Because the active component of soy for cholesterol reduction had not previously been identified, it could not be selected for in soy products. Thus, formerly, a person would have needed to eat large amounts of soy every day to see even a small decrease in cholesterol. Soy compositions are now provided with increased lunasin concentration, allowing for smaller doses, improved efficacy and more consistent results of treatment.

Further, processing and packaging problems related to providing large amounts of soy to individuals are addressed, and a variety of formulations are now available.

Studies show that lunasin can enter mammalian epithelial cells through its RGD cell adhesion motif, bind preferentially to deacetylated histones and inhibit histone H3 and H4 acetylation (20). There is growing evidence that cellular transformation, responses to hormones and dietary and environmental effects involve epigenetic changes in gene expression, which are modulated by the reversible processes of DNA methylation-demethylation and histone acetylation-deacetylation (21, 22).

Lunasin is the first natural substance to be identified as a histone acetylase inhibitor, although it does not directly affect the histone acetylase enzyme. It inhibits H3 and H4 acetylation by binding to specific deacetylated lysine residues in the N-terminal tail of histones H3 and H4, making them unavailable as substrates for histone acetylation (20.) The elucidation of the mechanism of action makes lunasin an important molecule for research studies to understand the emerging role of epigenetics and chromatin modifications in important biological processes.

The study on the effect of lunasin on prostate carcinogenesis at the University of California at Davis revealed the effects of lunasin on histone H4 modifications and the up regulation of chemopreventive genes, (23). However, the specific effect of lunasin binding to deacetylated H3N-terminal tail and the inhibition of H3 histone acetylation in biological systems has not yet been investigated.

Most circulating cholesterol in the blood is synthesized internally, thus the internal production of cholesterol as catalyzed by HMG-CoA reductase (the rate limiting enzyme for cholesterol biosynthesis) and the amount of LDL receptors in liver cell membranes are important factors in modulating LDL cholesterol levels (33).

To determine the specific biological effect of lunasin binding to deacetylated histone H3 and inhibition of acetylation, the induction of genes involved in cholesterol biosynthesis by the sterol regulatory element binding proteins (SREBP) was used as a biological model. This biological model was chosen because activation of SREBPs by sterol depletion results in the increased acetylation of histone H3, but not histone H4, by the histone acetylase enzyme P300/CBP-Associated Factor (PCAF), in chromatin proximal to the promoter/regulatory sequences of HMG-CoA reductase (the rate limiting enzyme for cholesterol biosynthesis) and the LDL receptor genes (24). Further, SREBP activation results in the increased recruitment of co-regulatory factors, Cyclic adenosine monophosphate Response Element Binding (CREB) to the promoter/regulatory sequence of the HMG-CoA reductase gene, and Sp1 to the promoter/regulatory sequence of LDL receptor gene (24).

Our studies on in vitro histone acetyltransferase (HAT) assays, (described below in EXAMPLE 8, show that lunasin significantly inhibits histone H3 acetylation by the histone acetylase enzyme, PCAF. Cell culture experiments using HepG2 liver cells show that synthetic lunasin can significantly reduce HMG-CoA reductase expression and increase LDL receptor gene expression in cholesterol-free media, (Example 1, below,) similar to the effects of statin type cholesterol-lowering drugs. Our studies have also shown that the increase in LDL receptor expression coincides with the increase in Sp1 expression in cholesterol-free media (Example 2, below.)

Without intending to limit the present invention to any particular mechanism or mode of action, a molecular mechanism of action is proposed, based on the experiments described, that lunasin reduces the acetylation of histone H3 by the histone acetylase enzyme, PCAF, required to activate expression of HMG-CoA reductase, and increases LDL receptor expression. Hence, lunasin can reduce total and LDL cholesterol levels by 1) inhibiting gene expression of HMG-CoA reductase, whose enzymatic activity is reduced by cholesterol-lowering statin drugs, and by 2) increasing LDL receptor expression, which increases clearance of LDL cholesterol in the blood.

Furthermore, the biological activity of lunasin, as shown in the examples, is further supported by large scale epidemiological and clinical data linking soy protein consumption with lower LDL cholesterol, and lower risk of cardiovascular disease (3). The identification of lunasin as the main component in soy protein that confers its cholesterol-lowering property paves the way for optimizing soy protein ingredients to maximize its heart-healthy benefits.

Previously published data demonstrates that lunasin content in different soy varieties, soy protein concentrates and soy protein isolates vary significantly from one preparation to another. (19.) Without intending to limit the invention to any particular mode of action or mechanism, it appears from the data that lunasin is the only bioactive agent from soy with a viable molecular mechanism of action that can explain the cholesterol-lowering property of soy protein (described below in EXAMPLES 1 and 2). The data also helps elucidate the widely divergent clinical results cited in the American Heart Association scientific report (16). Because we now know that lunasin is present in varying amounts in various soy protein preparations (19), it appears that the unpredictable results with respect to cholesterol lowering effects and the absence of dose dependent effects in previous studies using soy protein isolates, even those that tested higher concentrations of soy protein, is likely due to either to variation in the amounts of lunasin or the absence of chymotrypsin inhibitors to protect the lunasin during digestion or a combination of the two factors.

Our surprising finding that lunasin reduces cholesterol in individuals and is the responsible component of soy for lowering LDL cholesterol is further supported by the experiments demonstrating that the highest rate of LDL cholesterol reduction in clinical testing (20-30% reduction) was reported when 50% soy flour was mixed with 50% soy protein concentrate (26, 27). Although the concentration and biological activity of lunasin in various commercially available sources vary, among the different sources of lunasin, soy protein concentrates have shown higher yield of bioactive lunasin in some experiments (see Example 4 and reference (19.) In a preferred embodiment of the present invention, soy protein concentrate is a source of lunasin for use in compositions and methods of the present invention.

The presence of soy flour in a soy protein mixture such as that used in the clinical trials mentioned above is here shown to provide protection to lunasin from digestion and degradation when ingested (see Example 5). Partial digestion of lunasin enriched seed extract blended with soy flour has also been shown to increase bioactivity of lunasin (Example 6.)

It is shown below that soy flour protects the biological activity of compositions containing lunasin from reduction in biological activity from the effects of digestion. We have also found that trypsin inhibitors, and particularly chymotrypsin inhibitors found in soy flour (34) protect the biological activity of compositions containing lunasin from adverse effects of digestion. Without intending to limit the invention to any mechanism or mode of action, it is believed that, in the clinical studies mentioned above, the presence of endogenous chymotrypsin inhibitors in soy flour may have operated to protect lunasin from digestion, and made the lunasin peptide more bioavailable in the liver and the blood of those individuals participating in the study, thereby providing the highest rate of LDL cholesterol reduction.

The cholesterol-lowering effect of soy protein can be further increased by developing formulations that optimize the proper adsorption and delivery of lunasin to the liver, which is needed to bring about significantly lower plasma LDL cholesterol levels in individuals. Preferred embodiments of the invention encompass compositions comprising lunasin in combination with soy flour or chymotrypsin or a combination of the two, methods of using and making such compositions.

Lunasin is the small subunit peptide of a cotyledon-specific 2S albumin. FIG. 1 shows the 2S albumin protein (SEQ. ID. NO. 1) and the small lunasin subunit (SEQ. ID. NO. 2). Lunasin has been shown that constitutive expression of the lunasin gene in mammalian cells disturbs kinetochore formation and disrupts mitosis, leading to cell death (18). When applied exogenously in mammalian cell culture, the lunasin peptide suppresses transformation of normal cells to cancerous foci that are induced by chemical carcinogens and oncogenes. To elucidate its chemopreventive mechanism of action, we have shown that lunasin (a) is internalized through its RGD cell adhesion motif, (b) colocalizes with hypoacetylated chromatin in telomeres at prometaphase, (c) binds preferentially to deacetylated histone H4, which is facilitated by the presence of a structurally conserved helical motif found in other chromatin-binding proteins, (d) inhibits histone H3 and H4 acetylation, and (e) induces apoptosis in E1A-transfected cells (20). Based on these results, a novel chemopreventive mechanism has been proposed wherein lunasin gets inside the nucleus, binds to deacetylated histones, prevents their acetylation and inhibits gene expression like those controlled by the Rb tumor suppressor and h-ras oncogene.

Microarray experiments demonstrate minimal to no negative genetic changes using lunasin. To determine the genetic changes associated with lunasin treatment, the gene expression profiles of non-tumorigenic (RWPE-1) and tumorigenic (RWPE-2) prostate cells treated with synthetic lunasin were assessed using micro array analysis. Results show that of the 14500 genes interrogated, 123 genes had a greater than two-fold change in expression in the cells exposed to 2 uM lunasin for 24 hours (23). Of these genes, 121 genes were up-regulated in RWPE-1 cells and only two genes were up-regulated in RWPE-2 cells. No genes were down-regulated in non-tumorigenic or tumorigenic epithelial cells treated with 2 uM lunasin. Genes that were up-regulated in RWPE-1 cells include genes that are involved in preventing cancer formation such as tumor suppression, pro-apoptosis, mitotic checkpoints and the control of cell division (23).

The micro array results of our experiments also suggest that lunasin can act as a transcriptional activator of genes that protect normal cells from transformation. These findings are in contrast to the previous mechanistic models suggesting that lunasin prevents normal cell transformation into tumors by inhibiting the acetylation of deacetylated histones H4 (20). It is believed that blocking the acetylation of these histones results in chromatin condensation and transcriptional silencing of oncogenes even in the absence or inactivation of tumor suppressors such as Rb (retinoblastoma protein). In a recent study, however, lunasin-treated mouse fibroblast 3T3 cells obtained from the National Institutes of Health (NIH 3T3 cells) (pre-treated for 24 hours) transfected with the E1A oncogene showed a five-fold increase in p21/WAF1/Cipi protein levels, eight days after E1A transfection (28). The protein p21/WAF1/Cipi is a potent and universal inhibitor of cyclin-dependent kinases, which are major control points of cell cycle progression (29). The micro array results did not show up-regulation of p21/WAF1/Cipi within 24 hours; however, the gene SP3, a transcriptional activator of p21/WAF1/Cip (30), was upregulated by lunasin at 24 hours, which can explain the later increase in expression of p21/WAF1/Cipi in the NIH 3T3 cells.

In addition, the microarray results help explain the 70% reduction of foci formation observed when C3H/T101/2 cells pre-treated with lunasin are exposed to the chemical carcinogens Dimethylbenzanthracene (DMBA) and MCA (20). A single 24 hour exposure of these cells to as little as 125 nM lunasin was sufficient to suppress foci formation in chemical carcinogenesis assays that lasted for six weeks (20). The 24 hour pre-treatment of C3H/T101/2 cells with lunasin is believed to up-regulate expression of chemopreventive genes that protect the cells from transformation induced by DMBA and MCA.

Bioinformatic analysis of the 121 genes up-regulated by lunasin in normal prostate cells shows that more than 25% of the genes are located from 0 to 2000 bp (10 nucleosomes away) from a CpG island which is highly significant from just random distribution of genes in the genome. It is possible that the loss of up regulation of these chemopreventive genes in the tumorigenic prostate cell line (RWPE-2) by lunasin is due to increased cytosine methylation and chromatin hypoacetylation of the CpG islands, which are characteristic of carcinogenesis.

Screening Assay

The invention further provides an in vitro assay that can be used to screen potential sources of lunasin or analogues, fragments or variants of lunasin for biologically active material useful in the methods of the present invention. In one embodiment of the present invention, core histones purified from acid-extracted proteins of HeLa cells and chicken erythrocyte cells as well as recombinant histone H3 (commercially available from Upstate/Millipore) are used as templates in histone acetylase (HAT) reactions using PCAF histone acetylase enzyme in the presence or absence of lunasin. In a preferred embodiment of the present invention, potential sources of lunasin, or analogues, fragments or variants of lunasin are screened as follows: the core histone template and the lunasin sample (10:1 w/w) are incubated in ice for 5 min and 25° C. for 10 min before solution is added to 1×HAT reaction mix, 1 uM acetyl CoA and 5 uL PCAF (based on recommended concentration from Upstate/Millipore). The mixture is incubated at 30° C. while shaking at 250 rpm for 1 hour. The reaction is stopped by adding Laemmli stop buffer (1:1 v/v) with beta-mercaptoethanol, boiling for 5 min. and quenching in ice for 15 min. The products of PCAF HAT reaction are run on 16% SDS-PAGE, blotted onto nitrocellulose membrane and immunostained with primary antibodies raised against diacetylated histone H3 (Ac-Lys 13+Ac-Lys14 H3) and/or Ac-Lys14 histone H3, followed by HRP-conjugated secondary antibody. Chemiluminescent signals from antibody complexes can be visualized using standard chemiluminescent reagents and exposed to Kodak BioMAX film, developed and spot densitometer measured by using digital scanner and UN-SCAN-IT software program from Silk Scientific (Orem, Utah).

This in vitro HAT assay can be used to determine biological activity of lunasin (see Example 5 and 6) derived from different sources without resorting to time consuming and expensive cell culture and/or animal experiments. The activation of HMG-CoA reductase gene expression by SREBP transcriptional activator requires the acetylation of histone H3 (24) and the ability of lunasin to inhibit histone H3 acetylation leads to reduced expression of HMG-CoA reductase and consequently reduced cholesterol biosynthesis in the liver.

Sources of Lunasin.

Naturally-occurring lunasin can be found in significant amounts in soybean seeds and from commercially available sources of soy protein (19) and its analogues from other seed sources such as barley (35) and wheat (36). Because of the biological role of lunasin in the DNA endoreduplication stage of seed development (18), lunasin and its analogues are expected to be found in the endosperm and cotyledons of other seed-bearing plants (angiosperms) as well.

Polypeptides of the present invention can be obtained in a number of ways that are well known in the art. For example, without intending to limit the scope of the invention to any particular method of obtaining polypeptides of the present invention, lunasin and its analogues, variants and fragments can be chemically synthesized using commercially automated procedures, including, without limitation, conventional Merrifield solid phase f-Moc or t-Boc chemistry, Methods for polypeptide purification are also well-known in the art, including, without limitation, cation and anion exchange chromatography, immunoaffinity chromatography and size exclusion chromatography. For some purposes, it is preferable to produce the polypeptide in a recombinant system.

Fragments of a protein can be produced in several ways, e.g., by recombinant means, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein).

Screening for lunasin peptide analogues, fragment and variants: The presence and quantity of lunasin peptide, its analogues, fragments and variants can be determined by immunostaining Western blots with the lunasin antibody raised against the bioactive carboxyl end of the lunasin peptide (see Example 3). The bioactivity of the lunasin peptide, its analogues, fragments and variants can be determined and quantitatively analyzed by conducting the in vitro HAT assay as described in Example 4 and Example 8.

Natural Sources of Lunasin.

Lunasin is found in nature and can be obtained from soybean seeds and from commercially available sources of soy protein (19) and its analogues from other seed sources such as barley (35) and wheat (36). For example, without intending to be limited to any method of obtaining lunasin, lunasin can be extracted from the following soy sources: soy flour in flakes or powder form, soy protein concentrates and soy protein isolates (see Example 3).

Soy flakes are generally produced by dehulling, defatting, and grinding the soybean and typically contain less than about 65% (by weight) soy protein on a moisture-free basis. Soy flakes also contain soluble carbohydrates, insoluble carbohydrates such as soy fiber, and fat inherent in soy. Soy flakes may be defatted, for example, by extraction with hexane. Soy flours, soy grits, and soy meals are produced from soy flakes by comminuting the flakes in grinding and milling equipment such as a hammer mill or an air jet mill to a desired particle size. The comminuted materials are typically heat treated with dry heat or steamed with moist heat to "toast" the ground flakes and inactivate anti-nutritional elements present in soy, including Bowman-Birk and Kunitz trypsin inhibitors, and other protease inhibitors.

In one embodiment of the present invention toasting is not performed under conditions that destroy the activity of protease inhibitors. In a preferred embodiment of the present invention toasting is not performed for a duration or at a heat sufficient to destroy the activity of the chymotrypsin inhibitors. Heat treating the ground flakes in the presence of significant amounts of water is avoided to prevent denaturation of the soy protein in the material and to avoid costs involved in the addition and removal of water from the soy material. The resulting ground, heat treated material is a soy flour, soy grit, or a soy meal, depending on the average particle size of the material. Soy flour generally has a particle size of less than about 150 .mu.m. Soy grits generally have a particle size of about 150 to about 1000 .mu.m. Soy meal generally has a particle size of greater than about 1000 .mu.m.

Soy protein concentrates typically contain from about 65% (by weight) to less than about 90% (by weight) soy protein on a moisture-free basis, with the major non-protein component being fiber. Soy protein concentrates are typically formed from defatted soy flakes by washing the flakes with either an aqueous alcohol solution or an acidic aqueous solution to remove the soluble carbohydrates from the protein and fiber.

Soy protein isolates, also referred to as isolated soy proteins, which are more highly refined soy protein materials, are processed to contain at least about 90% (by weight) soy protein on a moisture-free basis and little or no soluble carbohydrates or fiber. Isolated soy proteins are typically formed by extracting soy protein and water soluble carbohydrates from defatted soy flakes or soy flour with an alkaline aqueous extractant. The aqueous extract, along with the soluble protein and soluble carbohydrates, is separated from materials that are insoluble in the extract, mainly fiber. The extract is typically then treated with an acid to adjust the pH of the extract to the isoelectric point of the protein to precipitate the protein from the extract. The precipitated protein is separated from the extract, which retains the soluble carbohydrates, and is dried after an optional pH adjustment step.

Extraction of Lunasin and Sources of Lunasin Enriched Compositions.

Lunasin and lunasin enriched compositions can be obtained from the low molecular weight albumin fraction of soy protein together with natural protease inhibitors found in soy (37, 38.) Extraction procedures for soy protease inhibitors can also be used to extract lunasin and obtain lunasin enriched compositions.

There are methods known in the art for extracting soy protease inhibitors. For example, see Konwinski et. al., U.S. Pat. No. 7,235,269, Kennedy et. al., U.S. Pat. Nos. 4,793,996, 5,217,717, 5,505,946, Konwinski, et. al., U.S. Patent Application No. 2003/0064,121, filed Apr. 3, 2003, Singe, U.S. Pat. No. 7,235,269, all of which are hereby incorporated by reference in their entirety. However, previous methods for extracting soy protease inhibitors have not been focused on optimizing the yield of lunasin. Improved biological activity of the compositions of the present invention can be obtained by prior screening of the source of starting material for the lunasin extraction for lunasin concentration prior to performing an extraction. In a preferred method of the present invention, potential sources of lunasin will be screened to determine lunasin concentration prior to being used for methods of the present invention.

The following additional examples of methods of obtaining lunasin enriched compositions are not intended to limit the present invention to any particular method of extracting lunasin. Defatted soy flour can be extracted with 60% ethanol, precipitated with cold acetone, followed by multi-step column chromatography. The protease inhibitors are soluble in 60% ethanol (together with other proteins). The protease inhibitors are then precipitated with cold acetone, spun down and re-dissolved in water to make a crude extract for further purification. (37). A modification of this procedure was used by Odani et al. (38) to isolate a soy extract that was used as starting material for further purification on CM-cellulose and DEAE-cellulose chromatography. In this procedure, defatted soy flour is extracted with 60% ethanol (4:1) at RT before adding 2 volumes of cold acetone, precipitate is redissolved in water, dialyzed with distilled water, pH is adjusted to 4.0 before further dialysis with 5 mM NaAcetate pH 4.0.

Another way of obtaining lunasin enriched is by extracting the low molecular weight fraction of soy protein (39, 40). In this procedure, total proteins are extracted from soy flour using buffered high salt solvent (0.1 M NaPhosphate buffer, pH 7.5, 0.5 M NaCl, 1 mM PMSF, 5 mM DTT). By dialyzing against distilled water, the soy albumins remain in solution because they are water soluble while the globulins which are insoluble in water precipitate out. Albumin solution is freeze dried and redissolved in smallest volume to obtain albumin concentrate, which should contain significant amounts of the lunasin peptide.

Further lunasin purification of low molecular weight albumins and protease inhibitor enriched soy extracts can be achieved by anion exchange or molecular exclusion chromatography and immunoaffinity chromatography. Examples of anion exhange resins: DEAE-sephadex, QAE-sephadex, DEAE-sepharose, QAE-sepharose, DEAE-sephacel, DEAE-cellulose, and QAE-cellulose. Examples of molecular exclusion resin: Sephadex G-25 (separates peptides 1-5 kDa, Sephadex G-50 (separates proteins 1.5-30 kDa). Immunoaffinity columns can be prepared by using lunasin antibody to capture lunasin peptide from soy protein fractions.

For Examples 3 and 4 below, a lunasin enriched seed extract was obtained as follows: soy protein concentrate found to contain biologically active lunasin in another experiment described herein was used as starting material in a one-step buffer extraction using 0.1×PBS followed by centrifugation to separate the supernatant. Around 2 volumes of acetone was added to supernatant and precipitate was separated by centrifugation with filter bags before vacuum drying to get a lunasin enriched seed extract. In certain embodiments of the present invention, instead of acetone precipitation, a variation to this procedure is to concentrate the supernatant after buffer extraction by heating to 75° C. with vacuum up to $1/10^{th}$ of original volume, followed by freeze drying to get a powder form of lunasin enriched seed extract.

Administration

The compositions can be administered using a number of different routes including oral administration, topical administration, transdermal administration, or injection directly into the body. Administration of compositions for use in the practice of the present invention can be systemic (i.e., administered to the subject as a whole via any of the above routes) or localized (i.e., administered to the specific location of the particular disease or pathological condition of the subject via any of the above routes).

The present methods, kits, and compositions can also be used in "combination therapy" with another composition or treatment that is indicated for treating or preventing a disorder related to or stemming from elevated cholesterol or lipid levels, such as, for example, a statin (e.g., lovastatin) an angiotensin converting enzyme inhibitor, an angiotensin II receptor antagonist, an antiarrhythmic, an anticholesteremic, a diuretic, a dopamine receptor agonist, a dopamine receptor antagonist, or a vasodilator, which are commonly administered to treat, prevent, or minimize the symptoms and complications related to this disorder. These drugs have certain disadvantages associated with their use, some of which may be ameliorated by a reduced dosage necessary to achieve a therapeutic effect when administered in combination with compositions of the present invention.

Dosing

In one exemplary embodiment of the present invention, a product containing an effective amount of lunasin peptides that lowers cholesterol levels in an individual that consumes the product is provided. It should be appreciated that the effective amount of lunasin will depend, at least in part, on the size, weight, health and desired goals of the individuals consuming the compositions. Accordingly, it is believed that in at least one embodiment, the effective amount of lunasin provided to the individual is 25 mg/kg to 100 mg/kg daily.

Depending upon the particular needs of the individual subject involved, the compositions of the present invention can be administered in various doses to provide effective treatment concentrations based upon the teachings of the present invention. Factors such as the activity of the selected compositions, the physiological characteristics of the subject, the extent or nature of the subject's disease or pathological condition, and the method of administration will determine what constitutes an effective amount of the selected compositions. Generally, initial doses will be modified to determine the optimum dosage for treatment of the particular subject. Suitable dosages can be chosen by taking into account any or all of such factors as the size, weight, health, age, and sex of the human or individual, the desired goals of the patient, the severity of the pathological condition for which the composition is being administered, the response to treatment, the type and quantity of other medications being given to the patient that might interact with the composition, either potentiating it or inhibiting it, and other pharmacokinetic considerations such as liver and kidney function. These considerations are well known in the art and are described in standard textbooks.

A therapeutically effective amount of any embodiment of the present invention is determined using methods known to pharmacologists and clinicians having ordinary skill in the art. For example, an effective amount can be determined subjectively by administering increasing amounts of the compositions of the present invention until such time the patient being treated shows reduction in cholesterol, total cholesterol, LDL cholesterol or lipid levels. Blood levels of the composition, cholesterol and lipid levels can be determined using routine biological and chemical assays and these blood levels can be matched to the route of administration. The blood level and route of administration giving the most desirable level of cholesterol reduction can then be used to establish an "effective amount" of the pharmaceutical composition for treatment.

This same method of titrating a composition in parallel with administration route can be used to ascertain a therapeutically effective amount of the compositions of the present invention for treating any and all disorders described herein. In addition, animal models as described below can be used to determine applicable dosages for a particular disease or pathological condition. Typically, dosage-effect relationships from in vitro or in vivo tests initially can provide useful guidance on the proper doses for subject administration.

In one embodiment of the present invention related to reducing or controlling cholesterol, LDL cholesterol or lipid levels, or the synthesis of cholesterol or LDL cholesterol, methods and compositions of the invention encompass a dose of a composition comprising lunasin, or a functionally equivalent variant, analogue or fragment of lunasin, of about 5 ng to about 1000 g, or about 100 ng to about 600 mg, or about 1 mg to about 500 mg, or about 20 mg to about 400 mg. Illustratively, a dosage unit of a composition of the present invention can typically contain, for example, without limitation, about 5 ng, 50 ng 100 ng, 500 ng, 1 mg, 10 mg, 20 mg, 40 mg, 80 mg, 100 mg, 125 mg, 150 mg, 200 mg, 250 mg, 300 mg, 350 mg, 400 mg, 450 mg, 500 mg, 550 mg, 600 mg, 700 mg, 800 mg, 900 mg, 1 g, 5 g, 10 g, 20 g, 30 g, or 40 g of a composition of the present invention. In certain preferred embodiments of the present invention, compositions of the present invention contain about 2.5 to 100 mg, preferably 5 to 50 mg, more preferably approximately 25 mg lunasin, or fragments, variants and analogues of lunasin.

Exemplary dosages for lunasin, or fragments, variants and analogues thereof, in accordance with the teachings of the present invention, range from 0.0001 mg to 200 mg, preferably, 2.5 mg to 100 mg, more preferably 25 mg to 50 mg for humans and other individuals having an average weight of 60 kg, although alternative dosages are contemplated as being within the scope of the present invention. In certain preferred embodiments of the present invention for compositions and methods for topical administration, lunasin, or fragments, variants and analogues thereof, is present at a level of between 25 ug/ml and 25 mg/ml, more preferably between 50 ug/ml and 1 mg/ml, more preferably between 100 ug/ml and 500 ug/ml, even more preferably, approximately 250 ug/ml. In certain preferred embodiments of the present invention for compositions and methods for oral administration, lunasin, or fragments, variants and analogues thereof, is provided to an individual at a level of between 0.01 mg/Kg and 100 mg/Kg body weight of an individual, preferably 0.05 mg/Kg and 50 mg/Kg, more preferably between 0.5 mg/Kg and 2.5 mg/Kg, and even more preferably between 0.2 mg/Kg and 1.5 mg/Kg.

A dose can be administered in one to about four doses per day, or in as many doses per day to elicit a therapeutic effect. The dosage form can be selected to accommodate the desired frequency of administration used to achieve the specified dosage, as well as the route of delivery.

The amount of therapeutic agent necessary to elicit a therapeutic effect can be experimentally determined based on, for example, the absorption rate of the agent into the blood serum, the bioavailability of the agent, and the potency for modulating the expression or action of HMG-CoA reductase and/or the LDL-receptor, and by monitoring reduction of total and LDL cholesterol. Determination of these parameters is well within the skill of the art.

Formulations.

The invention also concerns formulations containing the compositions of the present invention. The products and compositions of the present invention can be used alone or in foods, powders, bars, capsules, shakes and other well known products consumed by individuals.

In one preferred embodiment the compositions of the present invention are together with a dietary suitable excipient, diluent, carrier, or with a food. In a preferred embodiment of the present invention, the formulation is in the form of a pill, tablet, capsule, powder, food bar or similar dosage form.

The formulations may be a variety of kinds, such as nutritional supplements, pharmaceutical preparations, vitamin supplements, food additives or foods supplemented with the specified compositions of the invention, liquid or solid preparations, including drinks, sterile injectable solutions, tablets, coated tablets, capsules, powders, drops, suspensions, or syrups, ointments, lotions, creams pastes, gels, or the like.

The formulations may be packaged in convenient dosage forms, and may also include other active ingredients, and/or may contain conventional excipients, pharmaceutically acceptable carriers and diluents. The inclusion of the compositions of the present invention in herbal remedies and treatments is also a preferred part of the invention.

Preferred formulations for topical applications of the compositions of the present invention for both pharmaceutical and cosmetic use will employ excipients that are suitable for topical application. Topical formulations typically are gels, salves, powders, or liquids, though controlled formulations which release defined amounts of active ingredient at the desired surface are also desirable. The formulations may contain materials which enhance the permeability of the active moieties through the epidermis. Such penetrants include, for example, DMSO, various bile salts, non-toxic surfactants and the like. Standard ingredients for cosmetic/pharmaceutical compositions are well known in the art; formulations for topical application of pharmaceuticals are found in Remington's Pharmaceutical Sciences, latest edition, Mack Publishing Co., Easton, Pa., incorporated herein by reference. Cosmetic formulations are widely varied and well known to practitioners.

In one preferred embodiment of the present invention, compositions for topical use of the active ingredients are contemplated, whether for strictly cosmetic or pharmaceutical/cosmetic purposes.

Some embodiments of the present invention encompass methods for treating one or more of the following diseases or conditions: elevated levels of cholesterol, total cholesterol, LDL cholesterol or lipids, a cancerous tumor, any disease associated with hyperlipidemia, including without limitation atherosclerosis, hypertension, obesity, diabetes and kidney diseases, comprising treating a patient suffering from one of these diseases or conditions with compositions containing biologically active levels of lunasin, or functionally equivalent fragments, variants or analogues thereof according to methods of the present invention. Another embodiment of the present invention encompasses methods comprising treating, individuals desiring to maintain a particular level of cholesterol, total cholesterol, LDL cholesterol or lipids with biologically active levels of lunasin, or functionally equivalent fragments, variants or analogues thereof according to methods of the present invention.

While the primary use of the materials of the invention is intended for humans, there may be instances where treatment is desired on domestic or farm animals or in experimental animals. Indeed, one aspect of the invention is the use of experimental animals to confirm the safety and efficacy of the compositions of the invention. Thus, products intended for use in humans may be applied to laboratory animals such as rats, mice or rabbits to confirm the ability of the individual preparation to reduce or control cholesterol levels and to assure that an individual preparation is not toxic. The use of the materials of the invention in the context of quality control, as just described, is part of the invention.

Methods of Preserving or Enhancing Lunasin Biological Activity.

In another exemplary embodiment of the present invention, a composition containing an effective amount of lunasin peptides or lunasin peptide derivatives and a composition comprising one or more protease enzyme inhibitors that together lower cholesterol levels in an individual that consumes the composition is provided.

Protease enzyme inhibitors act to protect lunasin from digestion, thereby facilitating absorption and delivery to the appropriate target areas. Examples of appropriate protease enzyme inhibitors include, but are not limited to, inhibitors of pancreatin, trypsin and chymotrypsin. It should be appreciated that the scope of the present invention includes the use of the lunasin and lunasin fragments, analogues and variants with any other composition or product that is known or believed to facilitate lunasin's absorption or delivery in an individual.

In yet another exemplary embodiment of the present invention, a method for lowering or reducing cholesterol levels in an individual is provided. The method includes providing a product containing an effective amount of lunasin peptides to an individual and claiming that the product lowers, reduces or maintains cholesterol, total cholesterol, LDL cholesterol or lipid levels in an individual that consumes the composition. It should be appreciated that the present invention includes claiming that the product lower, reduces or maintains cholesterol, total cholesterol, LDL cholesterol or lipid levels in an individual that consumes the composition in a variety of ways, including but not limited to, through suggestion or explicitly stating it through written, verbal or electronic means.

In one aspect of at least one embodiment of the present invention, the lunasin peptides are obtained from soy. In another aspect of at least one embodiment of the present invention, the lunasin peptides are obtained from other seed bearing plants or a combination of soy and other seed bearing plants. Seed bearing plants containing sufficient amounts of lunasin are well known in the art.

In yet another aspect of at least one embodiment of the present invention, the lunasin peptides or lunasin peptide derivatives are obtained by producing, extracting and purifying lunasin peptides or lunasin peptide derivatives using recombinant DNA techniques or otherwise obtaining isolated lunasin peptides. In yet another aspect of at least one embodiment of the present invention, the lunasin peptides or lunasin peptide derivatives are obtained by synthetic polypeptide production. These methods of obtaining lunasin are well known in the art.

Partial Digestion of Lunasin.

A surprising discovery of the present invention is that rather than reducing or destroying the biological activity of lunasin, partial digestion of lunasin can actually enhance or increase the biological activity of lunasin. (See FIG. 8 and Example 6, below.) Therefore, a preferred embodiment of the present invention encompasses partially digested biologically active lunasin peptides.

Figure 8:
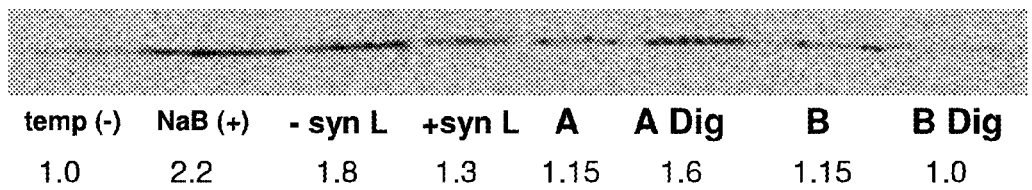
FIG. 8 is a photograph of a Western blot analysis showing the effects of digestion with pancreatin on biological activity of the lunasin enriched soy concentrate in the presence or absence of soy flour. The HAT bioactivity assay was conducted using acid extracted core histones from HeLa cells as a template/negative control (temp (−)) for the PCAF catalyzed HAT reaction. Core histones from sodium butyrate (NaB) treated HeLa cells were used as a positive control. The inhibitory effect of synthetic lunasin (+synL) on histone H3 acetylation by PCAF was used to compare the effect of LeSC (A), digested LeSC (A dig), LeSC+SF (B) and digested LeSC+SF (B dig). The numbers below the legend indicate relative densitometer readings normalized using immunosignal from the HeLa core histone template (temp (−)). Low numbers indicate biological activity.

The partial digestion of lunasin-enriched soy protein blended with soy flour (LeSC+SF) by pancreatin digestive enzyme increases the bioactivity of the lunasin peptide (FIG. 8.) This has practical application in the preparation of lunasin enriched seed extract for topical applications.

Synthetic lunasin has been shown to reduce skin tumor formation in mice when applied topically using ethanol as the delivery system (20.) By using partially digested biologically active lunasin in a topical formulation with an appropriate excipient, it is possible to increase the efficacy of lunasin for applications such as reducing skin tumor and cancer formation, actinic keratosis, rosaceae, age and sun spots and other skin diseases associated with abnormal cell division and proliferation. This formulation can also be used for topical delivery of lunasin to reduce cholesterol levels and to treat other cholesterol related diseases, such as, without limitation, atherosclerosis, hypertension, obesity and diabetes.

The presence of soy flour has been shown to protect lunasin's biological activity during digestion. (See Example 5.) Without intending to limit the present invention to any particular mechanism or mode of action, it is believed that the presence of soy flour during digestion protects lunasin from total digestion, but allows for partial digestion that increases lunasin's biological activity.

One embodiment of the present invention is a partially digested lunasin peptide, fragment variant or analogue thereof. A preferred embodiment of the present invention is a partially digested lunasin peptide, fragment variant or analogue thereof in combination with soy flour. Another preferred embodiment of the present invention is a partially digested lunasin peptide, fragment, variant or analogue thereof in a formulation appropriate for topical application. Another preferred embodiment of the present invention is a method of treating skin disorders comprising topically applying a partially digested lunasin peptide, analogue, variant or fragment thereof to a patient in need of such treatment.

It should be understood that the foregoing discussion, embodiments and examples merely present a detailed description of certain preferred embodiments. It will be apparent to those of ordinary skill in the art that various modifications and equivalents can be made without departing from the spirit and scope of the invention.

The following non-limiting examples are provided to better illustrate the present invention. The examples are not intended to limit the scope of the present invention and they should not be so interpreted. Other procedures and adaptations will be apparent to one of ordinary skill in the art upon views these reaction schemes and the structures of the compositions according to the invention. Such procedures are deemed to be within the scope of the present invention. Amounts are in weight parts or weight percentages unless otherwise indicated. All of the cited patents and publications are incorporated herein by reference.

EXAMPLES

The following examples are provided in order to demonstrate and further illustrate certain preferred embodiments and aspects of the present invention and are not to be construed as limiting the scope thereof.

Example 1

Experiments Demonstrating that Lunasin Lowers LDL and Total Cholesterol Levels

The lowering of serum cholesterol by statin drugs is achieved by competitively inhibiting the HMG-CoA reductase, the rate limiting enzyme in the body's metabolic pathway for synthesis of cholesterol. By reducing endogenous cholesterol synthesis, statins also cause liver cells to up regulate expression of the LDL receptor, leading to increased clearance of low-density lipoprotein (LDL) from the bloodstream (25). In 1985, Michael Brown and Joseph Goldstein received the Nobel Prize in Medicine for their work in clarifying this LDL-lowering mechanism.

Transcriptional regulation of HMG-CoA reductase and LDL receptor is controlled by the Sterol Regulatory Element-Binding Protein-1 and -2 (SREBP). This protein binds to the sterol regulatory element (SRE) located on the 5' end of the reductase and the LDL receptor genes. When SREBP is inactive, it is bound to the ER or nuclear membrane. When cholesterol levels fall, SREBP is released from the membrane by proteolysis and migrates to the nucleus, where it binds to the SRE to up regulate transcription of HMG-CoA reductase and LDL receptor (24, 25).

In cell culture of HepG2 liver cells, it is possible to activate SREBP and increase the expression of HMG-CoA reductase and LDL-receptor by removing cholesterol in the growth media. This can be achieved by exposing the cells to serum-free media for 24 hours (31, 32).

The following related experiments were performed to evaluate the effect of lunasin on HMG-CoA reductase expression and LDL-receptor expression.

In the first experiment, HepG2 cells ($1 \times 10^6$) were treated with or without 10 uM synthetic lunasin in DMEM with 10% FBS for 24 hours before growth media was replaced with cholesterol-free media to activate SREBP. After 24 hours, total protein was extracted and 10 ug protein was loaded onto 10% Tris-glycine gels, electroblotted onto nitrocellulose membrane, and immunostained with primary antibodies raised against HMG-CoA reductase and actin (to show equal loading of proteins). Spot densitometer values are obtained by digital scanning and Un-Scan It software, and represent mean and standard deviation of data from three separate experiments. The results are shown in FIG. 2.

In the second experiment, HepG2 cells ($1 \times 10^6$) were treated with or without 10 uM synthetic lunasin in DMEM with 10% FBS for 24 hours before growth media is replaced with cholesterol-free media to activate SREBP. After 24 hours, total protein was extracted and 10 ug proteins loaded onto 10% Tris-glycine gels, electroblotted onto nitrocellulose membrane, and immunostained with primary antibodies raised against LDL-receptor and actin (to show equal loading of proteins). Spot densitometer values were obtained by digital scanning and Un-Scan It software, and represent mean and standard deviation of data from three separate experiments. The results are shown in FIG. 3.

Figure 3:
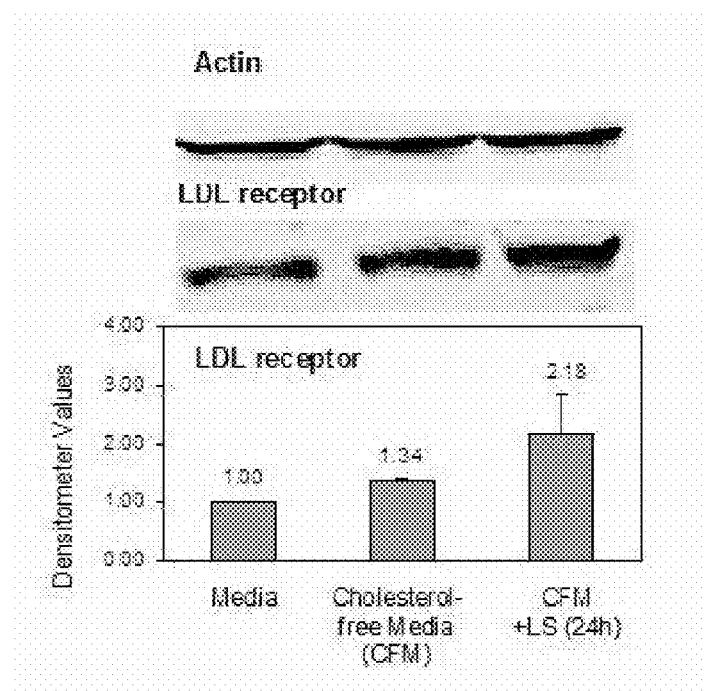
FIG. 3 is a photograph of a Western blot analysis (top) and a table (below) showing densitometer values indicating the relative levels of expression of LDL receptor in HepG2 cells that were (CFM+LS(24)) or were not (CFM) treated with lunasin for 24 hours prior to incubation in cholesterol free media (CFM) for 24 hours to activate SREBP. After incubations, total protein was extracted and 10 ug protein was loaded onto 10% Tris-glycine gels, electroblotted onto nitrocellulose membrane, and immunostained with primary antibodies raised against LDL-receptor and actin (to show equal loading of proteins.) Spot densitometer values represent mean and standard deviation of data from three separate experiments.

FIGS. 2 and 3 show the upregulation of HMG-CoA reductase (98% increase) and LDL-receptor (34% increase) when HepG2 cells are grown in cholesterol-free media for 24 hours.

However when lunasin is added to the cholesterol-free media, the expression of the HMG-CoA reductase is reduced by more than 50% (FIG. 2), while the expression of LDL-receptor has increased by more than 60% (FIG. 3).

This effect of lunasin is similar to statin drugs that reduces endogenous cholesterol synthesis by inhibiting HMG-CoA reductase activity, which leads to increased LDL receptor expression. However, while it is not intended that the present invention be limited to any precise mechanism or mode of action, the mode of action of lunasin is believed to differ from statin drugs in that it appears to inhibit expression of HMG-CoA reductase at the transcriptional level, rather than on inhibiting its enzyme activity. Like statin drugs, lunasin up regulates the expression of LDL-receptor gene. Again, while it is not intended that the present invention be limited to any precise mechanism or mode of action, the contrasting effect of lunasin on these two SREBP-controlled genes can be explained by the selective recruitment of different co-regulatory transcription factors to two separate cholesterol-regulated promoter/regulatory sequences.

Example 2

Lunasin's Effect on Expression of Sp1 Coactivator

Unlike HMG-CoA reductase, SREBP activation of LDL-receptor by sterol depletion requires increased recruitment of Sp1 co-activator to a site adjacent to SREBP in the promoter/regulatory sequence of LDL-receptor gene (25). As shown in FIG. 3, the up regulation of LDL-receptor by lunasin (LS) in cholesterol-free media may be due to increased availability and recruitment of the Sp1 coactivator to the LDL-receptor promoter/regulatory sequence. To test this hypothesis, the level of Sp1 was determined in lunasin-treated growth media and cholesterol-free media by Western analysis using Sp1 antibody, as follows: HepG2 cells ($1\times10^6$) were grown from confluence in DMEM with 10% FBS for 24 hours before growth media was replaced with fresh growth media or cholesterol-free media (to activate SREBP) and treated with, or without 10 uM synthetic lunasin. After 24 hours, total protein was extracted from each treatment and 10 ug protein loaded onto 10% Tris-glycine gels, electroblotted onto nitrocellulose membrane, and immunostained with primary antibodies raised against Sp1 and actin (to show equal loading of proteins). Spot densitometer values were obtained by digital scanning and Un-Scan It software and represent data from one experiment. The results are shown in FIG. 4.

Figure 4:
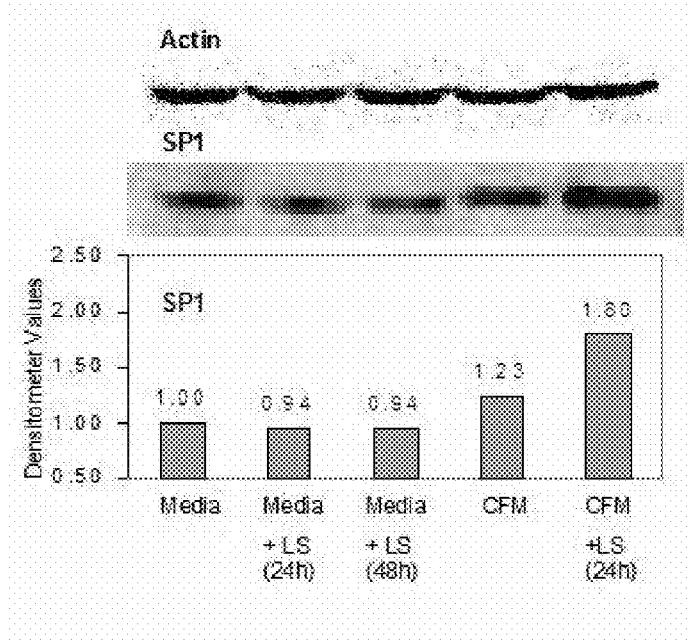
FIG. 4 is a photograph of a Western blot analysis (top) and a table (below) showing densitometer values indicating the relative levels of expression of Sp1 in HepG2 cells that were grown from confluence in growth media for 24 hours before growth media was replaced with fresh growth media (Media), media with lunasin (Media+LS) or cholesterol free media with lunasin (CFM+LS) or without lunasin (CFM). Samples were then incubated for 24 or 48 hours as indicated. After incubations, total protein was extracted and 10 ug protein was loaded onto 10% Tris-glycine gels, electroblotted onto nitrocellulose membrane, and immunostained with primary antibodies raised against Sp1 and actin (to show equal loading of proteins.) Spot densitometer values represent data from one experiment.

FIG. 4 shows that Sp1 levels in control and lunasin-treated growth media were not significantly different. However, Sp1 levels increased in cholesterol-free media by 23%, compared to the growth media. The addition of lunasin in the cholesterol-free media further increased Sp1 levels by almost 60%, which closely mirrors the increase in LDL-receptor levels in lunasin-treated, cholesterol-free media.

The data from these experiments indicate that the increase in LDL-receptor expression by lunasin in sterol-depleted media could be attributed to the increased availability of the Sp1 transcriptional co-activator. Also, the inhibition of HMG-CoA reductase expression by lunasin lowers intracellular cholesterol levels that keep SREBP activated, resulting in the upregulation of LDL receptor expression. Therefore, the data shows that lunasin inhibits the expression of HMG-CoA reductase, the rate limiting enzyme in the body's metabolic pathway for synthesis of cholesterol, and at the same time increases the expression of the LDL receptor, leading to increased clearance of low-density lipoprotein (LDL) from the bloodstream, which will lower total and LDL cholesterol in an individual.

Most circulating cholesterol in individuals is synthesized internally, on average 1000 mg/day compared to 200-300 mg/day from intestinal intake in a human diet. Thus the internal production of cholesterol, as catalyzed by HMG-CoA reductase and the amount of LDL receptors in liver cell membranes, is the single most important factor in modulating cholesterol levels in individuals. Accordingly, these experiments demonstrate that an effective amount of lunasin reduces both LDL and total cholesterol levels in an individual.

Example 3

Lunasin can be Extracted from Commercial Sources of Soy Protein

Lunasin has been found in significant amounts from commercial sources of soy protein (19) and its analogues from other seed sources such as barley (4) and wheat (5). To identify preferred sources for the starting raw material that can be used to obtain lunasin enriched seed extract, several commercially available soy protein products were screened for the presence of lunasin.

The procedure used was as follows: approximately 500 mg of soy protein samples (A-E) obtained from different commercial sources (Solae, St. Louis, Mo.) were dissolved in 50 mL of aqueous phosphate buffer (pH 7.2) by shaking for 1 hour at room temperature. Samples were centrifuged at 2500 rpm for 30 minutes and the aqueous fraction separated and put in separate tubes. Protein concentrations were measured by Bradford assay and around 20 ug of total protein were loaded onto two Bio-Rad Laboratories (Hercules, Calif.) 16% Tris-Tricine gels. One of the SDS-PAGE gels (I) was stained with Coomasie blue and destained before digital imaging. The 5 kDa lunasin band is indicated by arrow. The other (II) is electroblotted onto nitrocellulose membrane and incubated with affinity-purified lunasin polyclonal antibody (Pacific Immunology, (Ramona, Calif.) followed by HRP-conjugated donkey anti-rabbit secondary antibody (Amersham Biosciences, Piscataway, N.J.). Lunasin immunosignals (indicated by arrow) are detected using the ECL Western blotting kit from Amersham.

Figure 5:
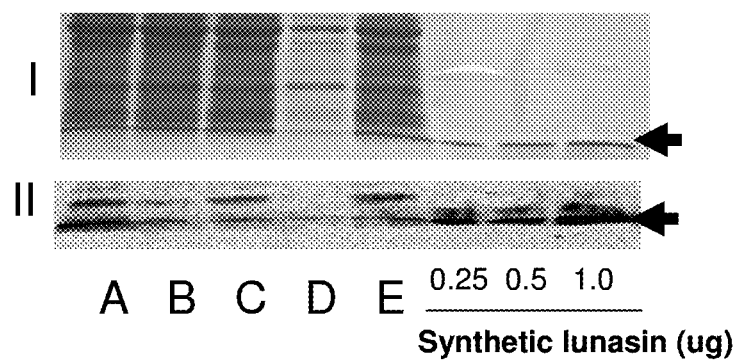
FIG. 5 is a digital image of a Coomasie blue stained SDS-PAGE gel (I) and a photograph of a Western blot analysis (II) showing 20 ug sized samples of soy protein extracted from five different commercial sources of soy protein (A-E) and 0.25 ug, 0.5 ug and 1.0 ug samples of synthetic lunasin. Each 5 kDa lunasin band is indicated by an arrow.

The results appear in FIG. 5. It is clear from the photograph that lunasin concentration varies dramatically from source to source. This assay is a useful tool in identifying sources of natural lunasin for use in the compositions and methods of the present invention. The soy concentrate (sample A in FIG. 5) that contained the most lunasin was used as a starting material in a buffer extraction procedure to produce a lunasin enriched seed extract that is referred to as "lunasin enriched soy concentrate" or "LeSC" in the following examples and the figures they reference.

Example 4

Formulated Lunasin Enriched Soy Concentrate (LeSC) and LeSC Supplemented with Soy Flour (SF) Contain Significant Amounts of Lunasin This experiment evaluated the amount of lunasin in lunasin enriched soy concentrate (LeSC) and LeSC supplemented with soy flour. Note that in certain embodiments of the present invention, lunasin enriched seed extract is obtained from soy isolate or other soy products rather than soy concentrate.

Lunasin enriched soy concentrate was produced by first identifying commercially available soy protein preparations that contain significant amounts of lunasin by Western blot analysis using lunasin polyclonal antibody, as described in Example 3. The soy protein concentrate identified to contain the most lunasin was used as starting material in a one-step buffer extraction procedure (0.1×PBS pH 7.2) followed by centrifugation to separate the supernatant. Two volumes of acetone were added to supernatant and precipitate was separated by centrifugation with filter bags before vacuum drying to get the lunasin enriched soy concentrate.

Efforts to make lunasin more resistant to undesired excessive digestion, improve its bioavailability, and retain its bioactivity when ingested, resulted in the discovery of at least one of the preferred embodiments of the present invention, a composition comprising lunasin enriched seed extract and soy flour.

In at least one embodiment of the present invention, compositions of the present invention comprising naturally derived lunasin can be optimized for use in particular methods of the present invention by varying the amount of total protein and lunasin content, which can be controlled by the amount of soy concentrate used, and varying the amount of lunasin protection from digestion, which can be controlled by the amount of soy flour used.

For food based items it is sometimes desirable to limit the amount of protease inhibitors in a product. For example, U.S. Patent Application No. 20070092633, filed Apr. 26, 2007, hereby incorporated by reference, teaches that part of the standard processing of some soy products includes heat treatment to inactivate anti-nutritional elements such as Bowman-Birk and Kuntz inhibitors. Therefore, in a preferred embodiment of the present invention, a composition comprising lunasin and soy flour is optimized through preparation methods described herein or known to one skilled in the art, to have a level of protease inhibitors sufficient to protect lunasin biological activity during digestion but not sufficient to have levels of anti-nutritional elements that are undesirable for oral use.

Clinical trials on a 50:50 blend of soy concentrate and soy flour led to a 20-30% reduction of LDL cholesterol (26, 27.) Those clinical trials were performed without the knowledge that lunasin is an active element in soy concentrate in reducing LDL cholesterol, and therefore did not control for the level of lunasin present in the blend. The present invention teaches improved methods of determining lunasin concentration in starting materials and final products of the present invention, so as to maximize the concentration of lunasin and therefore the activity of compositions of treatment in cholesterol related applications. In at least one preferred embodiment of the present invention the ratio of soy flour to lunasin enriched seed extract is between 10:90 and 50:50, more preferably between 20:80 and 40:60, more preferably approximately 30:70 soy flour:soy concentrate. In a preferred embodiment of the present invention, the ratio of soy flour to lunasin enriched seed extract is that which provides a biologically active concentration of lunasin and as well as sufficient protection from digestion by soy flour.

In the following several experiments, soy flour (SF) was added to the starting soy concentrate (at a 30:70 w/w mixture) before buffer extraction with 0.1×PBS pH 7.2 and acetone precipitation to produce lunasin enriched soy concentrate plus soy flour (LeSC+SF.)

Figure 6:
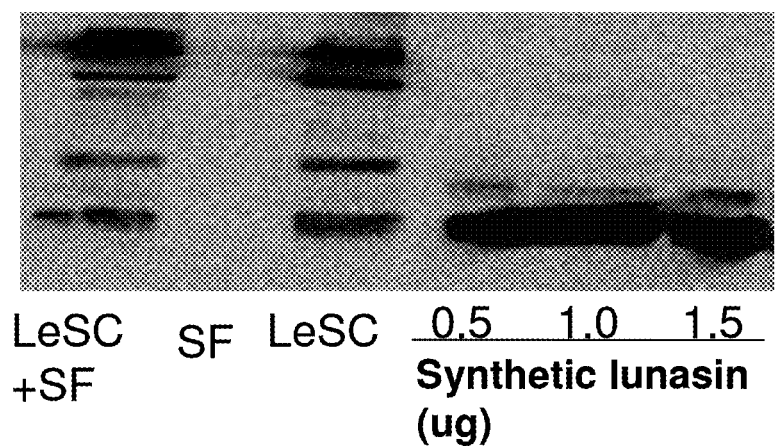
FIG. 6 is a photograph of a Western blot analysis of the protein content, and of particular interest, the lunasin content, of an enriched lunasin seed extract, specifically a formulated lunasin enriched soy concentrate (LeSC) soy flour (SF) and LeSC supplemented with soy flour (LeSC+SF) (see Example 4, below, for formulation and development of LeSC and LeSC+SF) compared with samples of synthetic lunasin of 0.5 ug, 1.0 ug and 1.5 ug.

The Western blotting analysis procedure used in this experiment was as follows: approximately 20 ug of total protein from LeSC, SF and the LeSC+SF were electrophoresed in 16% Tris-Tricine gels and electroblotted onto nitrocellulose membrane. Blots were incubated with lunasin polyclonal antibody followed by HRP-conjugated anti-rabbit secondary antibody before lunasin immunosignals were detected with the ECL kit. Both LeSC and LeSC+SF contained significant amounts of lunasin, as shown in FIG. 6.

Example 5

Figure 7:
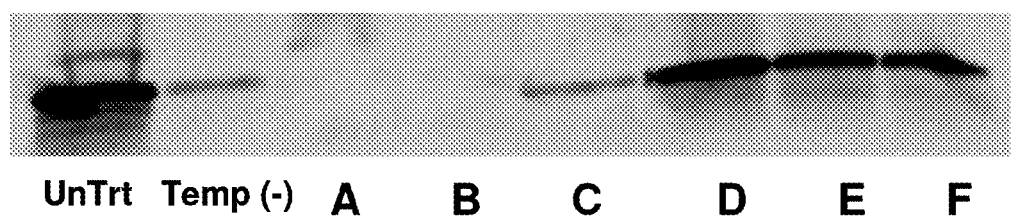
FIG. 7 is a photograph of a Western blot analysis showing the effect of digestion with pancreatin on the biological activity of various extracts, concentrates, and isolates of soy protein. A histone acetyltransferase (HAT) assay was used to determine biological activity. The lanes represent: LeSC (A), LeSC+SF (B), digested LeSC+SF (C), digested LeSC (D), digested soy protein isolate (E) and digested soy concentrate (F). The core histone from chicken erythrocyte is used as the negative control lane and the template (Temp-) histone for the HAT assay. The positive control lane corresponds to the untreated (Untrt) template core histones in a HAT assay which results in maximum histone acetylation. Low signal indicates that the sample was bioactive because it prevented the acetylation of histone H3. Strong signal indicates that the sample was inactive, thus failing to impact levels of histone H3 acetylation.

Lunasin Enriched Seed Extract Combined with Soy Flour Retains Bioactivity Even when Digested with Digestive Enzymes Biological activity of LeSC (A), LeSC+SF (B), digested LeSC+SF (C), digested LeSC (D), digested soy protein isolate (E) and digested soy concentrate (F) was measured using the H3 histone acetyltransferase (HAT) assay (see Example 8.) Around 100 mg total protein of LeSC, LeSC+SF, soy protein isolate and soy concentrate were digested by mixing pancreatin (Sigma Life Sciences, Saint Louis, Mo.) at 1:1 (w/w) and incubating for 30 min. at 40° C. To confirm that the HAT assay is working, treatment with synthetic lunasin (+synL) was included. Synthetic lunasin reduced acetylation of histone H3 by the histone acetylase enzyme, PCAF, using core histones isolated from chicken erythrocyte (Upstate/Millipore, Billerica, Mass.) as template for the HAT assay. Around 10 ug of sample protein was incubated with 1 ug of core histones before undergoing HAT reaction with PCAF enzyme and acetyl CoA substrate. Reaction products were run on 16% Tris-Tricine gels and electroblotted onto nitrocellulose membrane. Blots were incubated with primary antibody raised against acetylated H3 (diacetylated at histone14 and histone10) and HRP-conjugated anti-rabbit secondary antibody before detecting signals using the ECL kit. Low signals indicated that the lunasin peptide was bioactive because it prevented the acetylation of histone H3. Strong signals indicated that the lunasin peptide had been digested and rendered inactive, thus failing to impact levels of histone H3 acetylation. The results are shown in FIG. 7.

There was significant reduction in H3 acetylation in the presence of synthetic lunasin compared to the untreated control. Both the LeSC (A in FIG. 7) and the LeSC+SF (B in FIG. 7) were able to significantly reduce H3 acetylation by PCAF, indicating that the lunasin found in both soy protein extracts is biologically active. Pancreatin digestion of LeSC+SF (C in FIG. 7) reduced the biological activity but not to the extent observed when LeSC alone is digested (D in FIG. 7). Like LeSC, soy protein isolate and soy concentrate that contain significant amounts of lunasin, did not show lunasin biological activity after pancreatin digestion (E and F in FIG. 7). These results indicate that the formulated LeSC+SF protects lunasin to a certain degree from pancreatin digestion, and allows lunasin to retain its biological activity.

Example 6

Partial Digestion of Formulated LeSC+SF Increases Biological Activity of Lunasin A confirmatory experiment to determine the biological activity of digested and undigested LeSC and LeSC+SF was conducted using a different core histone template. This time we used the core histones extracted from HeLa tumor cells. Unlike the chicken erythrocyte cells, core histones from sodium butyrate treated HeLa cells are commercially available (Upstate/Millipore, Piscataway, N.J.), and can be used as a positive control for histone acetylation. The core histones isolated from untreated HeLa cells were used as a negative control (low levels of histone acetylation) and as template for the HAT assay.

The HAT bioactivity assay was conducted using acid extracted core histones from HeLa cells (Upstate/Millipore) as a template (temp (−) control) for the PCAF catalyzed HAT reaction. Core histones from sodium butyrate (NaB) treated HeLa cells were used as a positive control since NaB is a histone deacetylase inhibitor known to increase histone acetylation. The inhibitory effect of synthetic lunasin (+synL) on histone H3 acetylation by PCAF was used to compare the effect of lunasin enriched soy concentrate (A), digested LeSC (A dig), LeSC+SF (B) and digested LeSC+SF (B dig). LeSC and LeSC+SF were partially digested by adding pancreatin at 1:0.5 (w/w) and incubating at 38° C. for 15 min. The numbers below the legend indicate relative densitometer readings normalized using immunosignal from the template (temp). Low numbers indicate presence of lunasin biological activity.

The results are shown in FIG. 8. Significant reduction in H3 acetylation in the presence of synthetic lunasin was seen. The undigested LeSC (A) and LeSC+SF (B) showed reduced levels of H3 acetylation, indicating that the natural lunasin found in these soy extracts was biologically active. Partial digestion of LeSC (A Dig) led to the loss of biological activity.

Surprisingly, partial digestion of LeSC+SF resulted in an increase in biological activity rather than a decrease. While it is not intended that the present invention be limited to any precise mechanism, it is believed that lunasin is covalently bound to high molecular weight protein complexes and that, with the protection of soy flour, partial digestion only breaks down these bonds and releases, but does not destroy, bioactive lunasin into the solution. In a preferred embodiment of the present invention, lunasin is partially digested prior to use. In another preferred embodiment of the present invention, soy flour is present when lunasin is partially digested.

LeSC+SF was partially digested by mixing it with freshly prepared pancreatin solution (10 ug/mL of distilled water) in a 1:0.5, (w/w) ratio. Mixture was incubated at 38° C. for 15 min. before proteases and digestive enzymes were inactivated by boiling for 5 min and then quenching in ice. Under these digestion conditions the lunasin in the LeSC soy extract was digested and inactivated (FIG. 8 Lane Adig) while that of LeSC+SF were more biologically active (FIG. 8 Lane B dig). However, the conditions for the partial digestion of LeSC+SF has to be determined empirically by analyzing digestion products for lunasin content (FIG. 6) and biological activity using the HAT assay (FIG. 8.)

Variations in the sources of pancreatin and protease enzymes, the age of the protease enzyme, or incubation conditions can lead to variability in digestion conditions. For example, the use of one month old preparations of pancreatin for partial digestion led to the degradation and loss of activity of lunasin under similar incubation conditions described above. Therefore, in a preferred embodiment of the present invention, acceptable ranges for concentration of and incubation time with the protease enzymes are determined using an assay such as the HAT assay used above to evaluate biological activity of the treated compositions. In a preferred embodiment of the present invention fresh pancreatin enzymes, incubated at 38° C. for 10 minutes. For every ug of lunasin extract use 0.5 ug pancreatin.

Example 7

Chymotrypsin Inhibitors (Chy) Protect the Bioactivity of Lunasin

To determine which protease inhibitors found in soy protects lunasin from digestion, soybean trypsin inhibitor and trypsin+chymotrypsin inhibitors were obtained from Sigma and mixed with LeSC on 1:1 w/w ratio. The mixtures were digested with pancreatin, and digestion products immunostained with lunasin antibody.

Details of the experiment are as follows. LeSC+soybean trypsin inhibitors (1:1 w/w) (Sigma) and LeSC+trypsin and chymotrypsin inhibitors (1:1 w/w) (Sigma) were digested with pancreatin (1:1 w/w) by incubating at 38° C. for 15 min. Digestion products and LeSC were analyzed by Western blot analysis (FIG. 9) using lunasin primary antibody and synthetic lunasin as standard controls.

Figure 10:
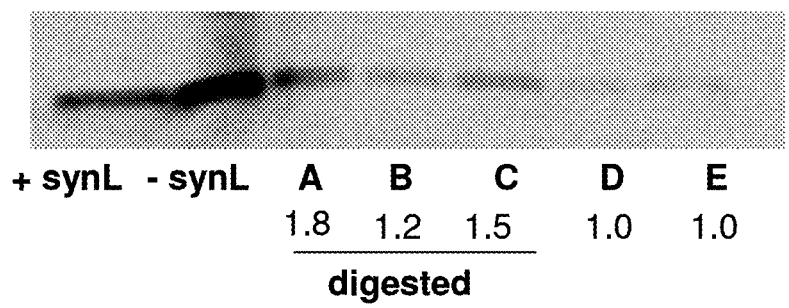
FIG. 10 is a photograph of a Western blot analysis showing the results of a HAT bioactivity assay was conducted using core histones from chicken erythrocyte cells as a template for the PCAF catalyzed HAT reaction (FIG. 6). The inhibitory effect of synthetic lunasin (+synL) as compared to the maximum histone acetylation in untreated negative control (−synL) on histone H3 acetylation by PCAF was used as a control to compare the effect of digestion on: lunasin enriched soy concentrate (LeSC) (A), LeSC with trypsin and chymotrypsin inhibitors (B), LeSC with trypsin inhibitors (C). Undigested LeSC (D), and undigested LeSC plus soy flour (E) are also included. The numbers below the legend indicate relative densitometer readings normalized using immunosignal from undigested LeSC (D). Low numbers indicate the presence of sample biological activity.

HAT bioactivity assay was conducted using core histones from chicken erythrocyte cells (Upstate/Millipore) as a template for the PCAF catalyzed HAT reaction (FIG. 10). The inhibitory effect of synthetic lunasin (+synL) on histone H3 acetylation by PCAF as compared to the negative untreated control (−synL) was used to compare the effect of digested LeSC (A), digested LeSC+try+chy (B), digested LeSC+try (C), undigested LeSC (D) and undigested LeSC+SF (E.) The numbers below the legend indicate relative densitometer readings normalized using immunosignal from undigested LeSC (D). Low numbers indicate the presence of lunasin biological activity.

Figure 9:
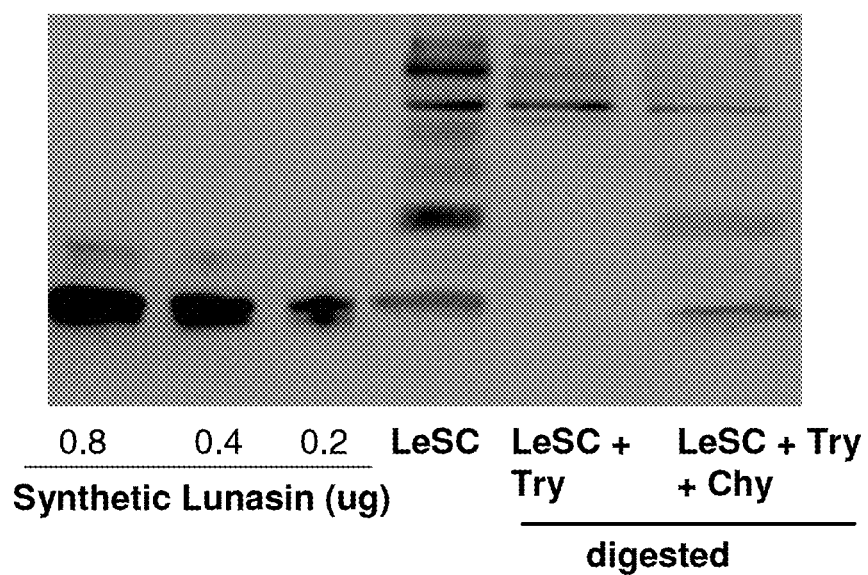
FIG. 9 is a photograph of a Western blot analysis showing the effect of pancreatin digestion on lunasin enriched soy concentrate in the presence and absence of trypsin and/or chymotrypsin inhibitors. Samples of lunasin enriched soy concentrate with trypsin inhibitors (LeSC+Try) and LeSC with both trypsin and chymotrypsin inhibitors (LeSC+Try+Chy) were digested with pancreatin and immunostained with lunasin antibody. Synthetic lunasin (0.8 ug, 0.4 ug, 0.2 ug) and undigested LeSC were included as a control.

The results in FIGS. 9 and 10 show that in the LeSC+trypsin+chymotrypsin inhibitors sample lunasin was better protected from digestion than in the LeSC+trypsin inhibitor sample. Likewise in HAT assays to determine lunasin biological activity, digestion of LeSC+trypsin+chymotrypsin inhibitors was significantly more bioactive than LeSC+trypsin inhibitor (FIG. 10). Pancreatin digestion of LeSC led to the loss of biological activity. These results indicate that the presence of chymotrypsin inhibitors with lunasin enriched seed extract both helps protect the biological activity of lunasin and helps protect lunasin from excessive digestion.

Example 8

Screening Assay to Determine Lunasin Biological Activity

Core histones purified from chicken erythrocyte cells were used as templates in histone acetylase (HAT) reactions using PCAF histone acetylase enzyme, in the presence or absence of around 2-10 uM lunasin. The core histone template and lunasin enriched soy concentrates (LeSC and LeSC+SF) were mixed (10:1 w/w) and incubated in ice for 5 min and 25° C. for 10 min before mixture was added to 1×HAT reaction mix, 1 uM acetyl CoA and 5 uL PCAF (based on recommended concentration from Upstate/Millipore). Reaction mixture was incubated at 30° C. while shaking at 250 rpm for 1 h. Reaction was stopped by adding Laemmli stop buffer (1:1 v/v) with beta-mercaptoethanol, and boiling for 5 min. before quenching in ice for 15 min. The products of PCAF HAT reaction were run on 16% SDS-PAGE, blotted onto nitrocellulose membrane and immunostained with primary antibodies raised against diacetylated histone H3 (Ac-Lys 13+Ac-Lys14 H3) followed by HRP-conjugated anti-rabbit secondary antibody. Chemiluminescent signals from antibody complexes were visualized using standard chemiluminescent reagents and exposed to Kodak BioMAX film, developed and spot densitometer measured by using digital scanner and UN-SCAN-IT software program from Silk Scientific (Orem, Utah). FIG. 7, Lanes A and B shows the reduction of H3 acetylation in the reaction mixtures treated with LeSc and LeSC+SF as compared to the untreated control, indicating that this screening procedure can determine the biological activity of lunasin enriched seed extracts and other compositions comprising lunasin or lunasin fragments, analogues or variants. In the same FIG. 7, it is also determined that digestion of LeSC (Lane D) eliminates biological activity but not that of LeSC+SF (Lane C) which shows only a partial reduction of biological activity. EXAMPLE 9

The in vivo activity of the presently described compositions, as well as treatment utilization of kits and treatment methods, may be optionally determined by either of the following procedures.

Male dogs (beagles, ranging from about 9 to about 14 kilograms, 1 to 4 years old) are fed a standard dog feed supplemented with 5.5% lard and 1% cholesterol. Baseline blood samples are drawn from fasted dogs prior to initiating the study to obtain reference values for plasma cholesterol. Dogs are then randomized to groups of five animals with similar plasma cholesterol levels. The animals are dosed in accordance with a treatment method described herein immediately prior to diet presentation for seven days. Blood samples are obtained 24 hours after the last dose for plasma cholesterol determinations. Plasma cholesterol levels are determined by a modification of the cholesterol oxidase method using a commercially available kit.

In an optional alternative procedure, hamsters are separated into groups of six and given a controlled cholesterol diet containing 0.5% cholesterol for seven days. Diet consumption is monitored to determine dietary cholesterol exposure. The animals are dosed in accordance with a treatment method described herein once daily beginning with the initiation of diet. Dosing is by oral gavage. All animals moribund or in poor physical condition are euthanized. After seven days, the animals are anesthetized by intramuscular (IM) injection of ketamine and sacrificed by decapitation. Blood is collected into vacutainer tubes containing EDTA for plasma lipid analysis and the liver is excised for tissue lipid analysis. Lipid analysis is conducted as per published procedures (e.g., Schnitzer-Polokoff et al., Comp. Biochem. Physiol., 99A, 4 (1991), pp. 665-670 and data is recorded as percent reduction of lipid versus control.

The above specification, examples and data provide a complete description of the manufacture and use of the compositions of the invention. While the products, compositions and related methods have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims. All the patents, journal articles and other documents discussed or cited above are herein incorporated by reference. All the patents, journal articles and other documents discussed or cited herein or listed below are herein incorporated by reference.

REFERENCES

The numeric references incorporated above correspond to the following list of published papers and abstracts. All of the below listed publications are herein incorporated by reference in their entirety to the same extent as if each individual publication was specifically and individually indicated to be incorporated by reference in its entirety.

1. Adlercruz H & Mazur W. Phyto-oestrogens and Western diseases. *Ann. Med.* 29: 95-1 20 (1997).
2. Zhang X., Shu X O, Gao Y T, Yang G., Li O, Li H, Jin F & Zheng W. Soy food consumption is associated with lower risk of coronary heart disease in Chinese women. *J. Nutr.* 133:2874-2878 (2003).
3. Anderson J W, Johnstone B M & Cook-Newell M E. Meta-analysis of effects of soy protein intake on serum lipids in humans. *N Eng J Med* 333: 276-282 (1995).
4. Anthony M S, Clarkson T B, Hughes C L et al. Soybean isoflavones improve cardiovascular risk factors without affecting the reproductive system of peripubertal rhesus monkeys. J Nutrl 26: 43-50 (1996).
5. Arjmandi B H, Khan D A, Juma S & Svanborg A. The ovarian hormone deficiency-induced hypercholesterolomia is reversed by soy protein and the synthetic isoflavone, ipriflavone. *Nutr. Res.* 17: 885-894 (1997).
6. Kirk E A, Sutherland P, Wang S A. Dietary isoflavones reduce plasma cholesterol and atherosclerosis in C57BL/6 mice but not LDL-receptor deficient mice. *J. Nutr.* 128: 954-959 (1998).
7. Crouse J R, Morgan T, Terry J G. A randomizing trial comparing the effect of casein with that of soy protein containing varying amounts of isoflavones on plasma concentrations of lipids and lipoproteins. *Arch Intern Med.* 159: 2070-2076 (1999).
8. Wong W W, Smith E O, Stuff J E. Cholesterol lowering effect of soy protein in normocholesterolomic and hypercholesterolomic men. *Am J Clin Nutr* 68: 1 385S-1389S (1998).
9. Greaves K A, Parks J S, Williams J K & Wagner J D. Intact dietary soy protein, but not adding an isoflavone-rich soy extract to casein, improves plasma lipids in ovariectomized cynomolgus monkeys. *J Nutr* 129:1585-1592 (1999).
10. Verrillo A, Teresa de A, Giarrusso P C. Soybean protein diets in the management of type II hyperlipoproteinaemia. *Atherosclerosis,* 54:321 (1985).
11. Kris-Etherton P & West S G. Soy protein with or without isoflavones: in search of a cardioprotective mechanism of action. *Am J Clin Nutr* 81:5-6 (2005).
12. Anthony M S. Phytoestrogens and cardiovascular disease: Where's the meat? *Arterioscler Thromb Vasc Biol* 22: 1245-1257 (2002).
13. Vega-Lopez S, Yeum K-J, Leckler J L. Plasma antioxidant capacity in response to diets high in soy or animal protein with or without isoflavones. *Am J Clin Nutr* 81: 43-49 (2005).
14. Oakenfull D G & Sidhu G S. Could saponins be a useful treatment for hypercholesterolaemia? *Eur J Clin Nutr* 44: 79-88 (1990).
15. Adams M R, Golden D L, Franke A A, Potter S M, Smith H S & Anthony M S. Dietary soy beta-conglycinin (7S globulin) inhibits atherosclerosis in mice. *J. Nutr.* 134: 511-516 (2004).
16. Sacks F M, Lichtenstein A., Van Horn L., Harris W., Kris-Etherton P. & Winston M. Soy protein, isoflavones and cardiovascular health. An American Heart Association Science Advisory for Professionals from the Nutrition Committee. Circulation. On-line publication, Feb. 21, 2006.

17. Galvez, A. F., Revilleza, M. J. R. & de Lumen, B. O. A novel methionine-rich protein from soybean cotyledon: cloning and characterization of cDNA. *Plant Physiol* 114:1 567 (1997).
18. Galvez, A. F. & de Lumen, B. O. A soybean cDNA encoding a chromatin-binding peptide inhibits mitosis of mammalian cells. *Nature Biotech.* 17: 495-500 (1999).
19. de Mejia E G, Vasconez M., de Lumen B O & Nelson R. Lunasin concentration in different soybean genotypes, commercial soy protein and isoflavone products. *J Agric Food Chem* 52: 5882-5887 (2004).
20. Galvez, A. F. Chen, N., Macasieb, J., & de Lumen, B. O. Chemopreventive property of a soybean peptide. *Cancer Res.* 61:7473-7478 (2001).
21. De Pinho, R. A. The cancer-chromatin connection. *Nature* 391: 533-536 (1998).
22. Kuzmin I. & Geil L. DNA methylation and chromatin modifications in cancer and development. *Int Arch Biosci* 2001: 1047-1 056 (2001).
23. Magbanua M, Dawson K, Huang L, Malyj W, Gregg J, Galvez A & Rodriguez R L. Nutrient-Gene Interactions Involving Soy Peptide and Chemopreventive Genes in Prostate Epithelial Cells, in *Nutritional Genomics—Discovering the Path to Personalized Nutrition*, J. Kaput and R. L. Rodriguez eds., Wiley and Sons, New Jersey (2005).
24. Bennett M K & Osborne T F. Nutrient regulation of gene expression by the sterol regulatory element binding proteins: Increased recruitment of gene-specific coregulatory factors and selective hyperacetylation of histone H3 in vivo. *PNAS* 97: 6340-6344 (2000).
25. Brown M S & Goldstein J L. Lowering plasma cholesterol by raising LDL receptors. *Atherosclerosis Suppl* 5: 57-59 (2004).
26. Sirtori C R, Gatti E, Mantero O, Conti F., et al. Clinical experience with the soybean protein diet in the treatment of hypercholesterolemia. *Am J Clin Nutr.* 32:1645-1658 (1979).
27. Descovich G C, Ceredi C., Gaddi A., Benassi M S, et al., Multicentre study of soybean protein diet for outpatient hyper-cholesterolaemic patients. *Lancet* 2:709-712 (1980).
28. Lam, Y., Galvez, A., and de Lumen, B. O. Lunasin suppresses E1A-mediated transformation of mammalian cells but does not inhibit growth of immortalized and established cancer cell lines. *Nutrition & Cancer,* 47:88-94 (2003).
29. Coqueret, O, New roles for p21 and p27 cell-cycle inhibitors: A function for each cell compartment? *Trends in Cell Biology,* 13:65-70, (2003).
30. Bruzzone, R., White, T. W., and Paul, D. L. Connections with connexins: The molecular basis of direct intercellular signaling. *European Journal of Biochemistry,* 238: 1-27 (1996).
31. Mullen E, Brown R M, Osborne T F & Shay N F. Soy isoflavones affect sterol regulatory element binding proteins (SREBPs) and SREBP-regulated genes in HepG2 cells. *J. Nutr.* 134: 2942-2947 (2004).
32. Gherardi E., Thomas K, Le Gras T D, Fitzsimmons C, Moorby C D & Bowyer D E. Growth requirements and expression of LDL receptor and HMG-CoA reductase in HepG2 hepatoblastoma cells cultured in a chemically defined medium. *J Cell Sci.* 103:531-539 (1992).
33. Brown M S & Goldstein J L. Lowering plasma cholesterol by raising LDL receptors. *Atherosclerosis Suppl* 5: 57-59 (2004).
34. Di Pietro C M & Liener I E. Soybean protease inhibitors in foods. *Journal of Food Science* 54: 606-609 (1989).
35. Jeong H J, Lam Y & de Lumen B O. Barley lunasin suppresses ras-induced colony formation and inhibits core histone acetylation in mammalian cells. *J Agric Food Chem.* 50:5903-5908 (2002).
36. Jeong H J, Jeong J B, Kim D S et al. The cancer preventive peptide lunasin from wheat inhibits core histone acetylation. *Cancer Lett.* 255:42-48 (2007).
37. Fratalli V. Soybean inhibitors. III. Properties of a low molecular weight soybean protease inhibitor. *J Biol Chem* 274:280 (1969).
38. Odani et al. Amino acid sequence of a soybean (*Glycine max*) seed polypeptide having a poly (L-aspartic acid) structure) *J Biol Chem* 262:10502-10505. (1987).
39. Kho, C. J. and de Lumen, B. O. Identification and isolation of methionine-cysteine rich protein fraction in soybean seed. *Plant Foods for Human Nutrition* 38: 287-296 (1988).
40. Revilleza M. J., Galvez A. F., Krenz D. C. and de Lumen B. O. An 8 kDa methionine-rich protein from soybean (*Glycine max*) cotyledon: Identification, purification and N-terminal sequence. *J Agric Food Chem* 44:2930-2935 (1996).

The invention claimed is:

1. A method for lowering cholesterol levels in an individual, comprising: (a) providing: (i) an individual desiring or needing to lower cholesterol levels and, (ii) a lunasin enriched composition comprising an effective amount of the peptide of SEQ ID NO 2; and (b) administering said composition to said subject.

2. The method of claim 1, wherein said peptide is obtained from soybean, wheat or barley.

3. The method of claim 1, wherein said peptide is obtained by producing, extracting and purifying said peptide using recombinant DNA techniques.

4. The method of claim 1, wherein said peptide is obtained by synthetic polypeptide production.

5. The method of claim 1, wherein said individual is a human.

6. The method of claim 1 wherein administering comprises oral ingestion of the lunasin enriched composition.

7. The method of claim 1, wherein the lunasin enriched composition is in the form of a capsule, tablet, powder, semi-solid formulation, liquid, gel, suspension, or aerosol spray.

8. The method of claim 1, wherein said lunasin enriched composition further comprises chymotrypsin inhibitor.

9. The method of claim 1, wherein said peptide is administered to said individual at between 0.05 mg/kg and 50 mg/kg daily.

10. The method of claim 1, wherein said individual is at risk for atherosclerosis, arterial sclerosis, myocardial infarction, heart attack, diabetes, coronary heart disease, angina pectoris or unstable angina.

11. The method of claim 1, wherein said lunasin enriched composition further comprises soy flour.

12. A method for treating or preventing cardiovascular disease comprising: providing: (i) an individual suffering from or at risk of developing cardiovascular disease, and, (ii) a lunasin enriched composition comprising an effective amount of the peptide of SEQ ID NO 2; and (b) administering said composition to said subject.

13. The method of claim 12, wherein said peptide is obtained from soybean, wheat or barley.

14. The method of claim 12, wherein said peptide is obtained by producing, extracting and purifying said compound using recombinant DNA techniques.

15. The method of claim 12, wherein said peptide is obtained by synthetic polypeptide production.

16. The method of claim 12, wherein said individual is a human.

17. The method of claim 12 wherein administering comprises oral ingestion of the lunasin enriched composition.

18. The method of claim 12, wherein the lunasin enriched composition is in the form of a capsule, tablet, powder, semi-solid formulation, liquid, gel, suspension, or aerosol spray.

19. The method of claim 12, wherein said lunasin enriched composition further comprises chymotrypsin inhibitor.

20. The method of claim 12, wherein said peptide is administered to said individual at between 0.05 mg/kg and 50 mg/kg daily.

21. The method of claim 12, wherein said individual is at risk for atherosclerosis, arterial sclerosis, myocardial infarction, heart attack, diabetes, coronary heart disease, angina pectoris or unstable angina.

22. The method of claim 12, wherein said lunasin enriched composition further comprises soy flour.

23. A method for lowering or reducing cholesterol levels in an individual, comprising: a) providing a lunasin enriched composition comprising an effective amount of the peptide of SEQ ID NO 2; and b) claiming that the product reduces cholesterol, total cholesterol, LDL cholesterol or lipid levels in an individual that consumes the composition.

24. The method of claim 23, wherein said peptide is obtained from soybean, wheat or barley.

25. The method of claim 23, wherein said peptide is obtained by producing, extracting and purifying said compound using recombinant DNA techniques.

26. The method of claim 23, wherein said peptide is obtained by synthetic polypeptide production.

27. The method of claim 23, wherein said individual is a human.

28. The method of claim 23 wherein said lunasin enriched composition is in the form of a capsule, tablet, powder, semi-solid formulation, liquid, gel, suspension, or aerosol spray.

29. The method of claim 23, wherein said lunasin enriched composition further comprises chymotrypsin inhibitor.

30. The method of claim 23, wherein said individual is at risk for atherosclerosis, arterial sclerosis, myocardial infarction, heart attack, diabetes, coronary heart disease, angina pectoris or unstable angina.

31. The method of claim 23, wherein said lunasin enriched composition further comprises soy flour.

32. A method of claim 23, wherein the effective amount of said lunasin enriched composition that lowers cholesterol levels in an individual is 0.05 mg/kg to 50 mg/kg daily.

33. A method for reducing cholesterol levels, comprising: providing to a human in need thereof a lunasin enriched composition comprising an effective amount of the peptide of SEQ ID NO 2.

34. The method of claim 1, wherein from 1 mg to 1 g of said lunasin enriched concentration is administered to said individual daily.

35. The method of claim 1, wherein from 100 mg to 500 mg of said lunasin enriched concentration is administered to said individual daily.

36. The method of claim 1, wherein a dose of from 2.5 mg to 100 mg of said peptide is administered to said individual.

37. The method of claim 36, wherein one to four doses of said peptide is administered to said individual daily.

38. The method of claim 1, wherein said peptide is administered to said individual at between 0.01 mg/kg and 100 mg/kg.

39. The method of claim 1, wherein said peptide is administered to said individual at between 0.05 mg/kg and 2.5 mg/kg per dose.

40. The method of claim 33, wherein from 1 mg to 1 g of said lunasin enriched concentration is administered to said individual daily.

41. The method of claim 33, wherein from 100 mg to 500 mg of said lunasin enriched concentration is administered to said individual daily.

42. The method of claim 33, wherein a dose of from 2.5 mg to 100 mg of said peptide is administered to said individual.

43. The method of claim 42, wherein one to four doses of said peptide is administered to said individual daily.

44. The method of claim 33, wherein said peptide is administered to said individual at between 0.01 mg/kg and 100 mg/kg.

45. The method of claim 33, wherein said peptide is administered to said individual at between 0.05 mg/kg and 2.5 mg/kg per dose.

* * * * *